(12) United States Patent
Bellomo et al.

(10) Patent No.: US 8,771,291 B2
(45) Date of Patent: Jul. 8, 2014

(54) DERMAL MICRO-ORGANS, METHODS AND APPARATUSES FOR PRODUCING AND USING THE SAME

(71) Applicant: Medgenics Medical Israel Ltd., Misgav (IL)

(72) Inventors: Stephen F. Bellomo, Zichron Yaakov (IL); Alex Okun, Abirim (IL); Yaron Fuerst, Kfar Vradim (IL); David Shalhevet, Kiryat Tivon (IL); Elisha Amir, Livnim (IL); Mordechay Bukhman, Carmiel (IL)

(73) Assignee: Medgenics Medical Israel Ltd., Misgav (IL)

( * ) Notice: Subject to any disclaimer, the term of this patent is extended or adjusted under 35 U.S.C. 154(b) by 0 days.

(21) Appl. No.: 13/686,939

(22) Filed: Nov. 28, 2012

(65) Prior Publication Data

US 2013/0090669 A1 Apr. 11, 2013

Related U.S. Application Data

(60) Continuation-in-part of application No. 13/369,329, filed on Feb. 9, 2012, which is a division of application No. 12/216,321, filed on Jul. 2, 2008, now Pat. No. 8,142,990, which is a continuation of application No. 10/834,345, filed on Apr. 29, 2004, now Pat. No. 7,468,242.

(60) Provisional application No. 60/466,793, filed on May 1, 2003, provisional application No. 60/492,754, filed on Aug. 6, 2003.

(51) Int. Cl.
*A61B 17/322* (2006.01)

(52) U.S. Cl.
USPC .......................................................... 606/132

(58) Field of Classification Search
USPC .................. 606/131, 132, 133, 184, 187, 167; 424/93.21
See application file for complete search history.

(56) References Cited

U.S. PATENT DOCUMENTS

| 376,511 A * | 1/1888 | Carter .......................... 131/255 |
| 1,516,071 A | 11/1924 | Apolant |

(Continued)

FOREIGN PATENT DOCUMENTS

| CA | 2279996 | 7/1998 |
| CN | 1310027 | 8/2001 |

(Continued)

OTHER PUBLICATIONS

Rubanyi. "The Future of Human Gene Therapy" Molecular Aspects of Medicine, 22:113-142, (2001).

(Continued)

*Primary Examiner* — Thomas McEvoy
*Assistant Examiner* — Julie A Szpira
(74) *Attorney, Agent, or Firm* — Pearl Cohen Zedek Latzer Baratz LLP; Mark S. Cohen

(57) ABSTRACT

Embodiments of the present invention provide Dermal Micro-organs (DMOs), methods and apparatuses for harvesting the same. Some embodiments of the invention provide a DMO including a plurality of dermal components, which substantially retain the micro-architecture and three dimensional structure of the dermal tissue from which they are derived. An apparatus for harvesting the DMO may include, according to some exemplary embodiments, a support configuration to support a skin-related tissue structure from which the DMO is to be harvested, and a cutting tool able to separate the DMO from the skin-related tissue structure. Exemplary embodiments of the invention provide a genetically modified dermal micro-organ expressing at least one recombinant gene product. Some embodiments of the invention provide methods and apparatuses for implanting a genetically modified DMO.

17 Claims, 16 Drawing Sheets

(56) References Cited

U.S. PATENT DOCUMENTS

| | | | |
|---|---|---|---|
| 3,076,461 A | 2/1963 | Meek et al. | |
| 3,470,782 A | 10/1969 | Acker. | |
| 3,613,242 A | 10/1971 | Hill et al. | |
| 4,353,888 A | 10/1982 | Sefton | |
| 4,391,909 A | 7/1983 | Lim | |
| 4,773,418 A | 9/1988 | Hettich | |
| 4,883,666 A | 11/1989 | Sabel et al. | |
| 4,892,538 A | 1/1990 | Aebisher et al. | |
| 5,106,627 A | 4/1992 | Aebisher et al. | |
| 5,266,480 A | 11/1993 | Naughton et al. | |
| 5,417,683 A | 5/1995 | Shiao | |
| 5,423,330 A * | 6/1995 | Lee | 600/566 |
| 5,477,862 A | 12/1995 | Haaga | |
| 5,670,148 A | 9/1997 | Sherwin et al. | |
| 5,693,064 A * | 12/1997 | Arnold | 606/184 |
| 5,817,034 A | 10/1998 | Milliman et al. | |
| 5,817,120 A * | 10/1998 | Rassman | 606/187 |
| 5,871,767 A | 2/1999 | Dionne et al. | |
| 5,888,720 A | 3/1999 | Mitrani | |
| 5,932,459 A | 8/1999 | Sittinger et al. | |
| 5,944,673 A | 8/1999 | Gregoire et al. | |
| 6,001,647 A | 12/1999 | Peek et al. | |
| 6,027,512 A * | 2/2000 | Bridges | 606/131 |
| 6,036,657 A * | 3/2000 | Milliman et al. | 600/564 |
| 6,039,760 A | 3/2000 | Eisenberg | |
| 6,059,807 A | 5/2000 | Boudjema | |
| 6,197,575 B1 | 3/2001 | Griffith et al. | |
| 6,303,136 B1 | 10/2001 | Li et al. | |
| 6,372,482 B1 | 4/2002 | Mitarni | |
| 6,461,369 B1 | 10/2002 | Kim | |
| 6,472,200 B1 | 10/2002 | Mitrani | |
| 6,485,721 B1 | 11/2002 | Yoshida et al. | |
| 7,067,496 B2 | 6/2006 | Saito et al. | |
| 7,468,242 B2 | 12/2008 | Bellomo et al. | |
| 7,621,934 B2 | 11/2009 | Bodduluri et al. | |
| 7,625,384 B2 | 12/2009 | Eriksson et al. | |
| 7,666,134 B2 | 2/2010 | Eriksson et al. | |
| 7,708,746 B2 | 5/2010 | Eriksson et al. | |
| 8,062,322 B2 | 11/2011 | Rassman et al. | |
| 8,211,134 B2 | 7/2012 | Oostman, Jr. | |
| 8,586,024 B2 | 11/2013 | Pearlman et al. | |
| 2002/0001580 A1 | 1/2002 | Hermonat et al. | |
| 2002/0068880 A1 | 6/2002 | Burbank et al. | |
| 2003/0086914 A1 | 5/2003 | Mitarni | |
| 2003/0124565 A1 | 7/2003 | Garfinkel et al. | |
| 2003/0152561 A1 | 8/2003 | Mitrani | |
| 2003/0152562 A1 | 8/2003 | Mitrani | |
| 2003/0157074 A1 | 8/2003 | Mitrani | |
| 2004/0157293 A1 | 8/2004 | Evans et al. | |
| 2004/0172045 A1 | 9/2004 | Eriksson et al. | |
| 2004/0230215 A1 | 11/2004 | Eriksson et al. | |
| 2005/0096687 A1* | 5/2005 | Rassman et al. | 606/187 |
| 2005/0188431 A1 | 8/2005 | Ivarie et al. | |
| 2006/0271070 A1 | 11/2006 | Eriksson et al. | |
| 2007/0038236 A1* | 2/2007 | Cohen | 606/187 |
| 2008/0090777 A1 | 4/2008 | Pearlman | |
| 2010/0042127 A1 | 2/2010 | Eriksson et al. | |
| 2010/0145360 A1 | 6/2010 | Eriksson et al. | |
| 2011/0264115 A1* | 10/2011 | Asrani et al. | 606/132 |

FOREIGN PATENT DOCUMENTS

| | | |
|---|---|---|
| DE | 29 39 057 | 4/1981 |
| DE | 34 32 897 | 3/1986 |
| EP | 1306426 | 5/2003 |
| EP | 1358857 | 11/2003 |
| JP | 233694/86 | 10/1986 |
| JP | 76399/99 | 3/1999 |
| JP | 2003-176213 | 6/2003 |
| JP | 2005/506084 | 3/2005 |
| JP | 08/196271 | 8/2008 |
| WO | WO 96/15225 | 5/1996 |
| WO | WO 9704720 | 2/1997 |
| WO | WO 97/08295 | 3/1997 |
| WO | WO 9715655 | 5/1997 |
| WO | WO 98/16158 | 5/1998 |
| WO | WO 99/06073 | 2/1999 |
| WO | WO 99/49807 | 7/1999 |
| WO | WO 99/43270 | 9/1999 |
| WO | WO 99/47678 | 9/1999 |
| WO | WO 00/49162 A2 | 8/2000 |
| WO | WO 01/00859 | 1/2001 |
| WO | WO 01/07098 | 2/2001 |
| WO | WO 01/08714 | 2/2001 |
| WO | WO 01/60424 | 8/2001 |
| WO | WO 03/002154 | 1/2003 |
| WO | WO 03/006669 | 1/2003 |
| WO | WO 03/020107 | 3/2003 |
| WO | WO 03/035851 | 5/2003 |
| WO | WO 03/039382 | 5/2003 |
| WO | WO/03049626 | 6/2003 |
| WO | WO 03/060062 | 7/2003 |
| WO | WO 2004/075764 | 9/2004 |
| WO | WO 2004/099363 | 11/2004 |
| WO | WO 2005/033273 | 4/2005 |
| WO | WO 2006/110843 | 10/2006 |
| WO | WO 2007/117488 | 10/2007 |
| WO | WO 2011/140497 | 11/2011 |

OTHER PUBLICATIONS

Orive et al. "Cell encapsulation: Promise and progress" Nature Medicine, 9(1):104-107, (2003).

Brill-Almon E. et al: "Ex vivo transduction of human dermal tissue structures for autologous implantation production and delivery of therapeutic proteins," Molecular Therapy, Academic Press, CA, USA, vol. 12, No. 2. pp. 274-282, (2005).

Hasson E. et al. "Solid tissues can be manipulated ex vivo and used as vehicles for gene therapy" Journal of Gene Medicine, vol. 7(7), pp. 923-935 , (2005).

Uitto et al. "Skin elastic fibres: regulation of human elastin promoter activity in transgenic mice". Ciba Foundation Symposium, vol. 192, pp. 237-253, (1995).

Wang et al. "Transgenic studies with a keratin promoter-driven growth hormone transgene: prospects for gene therapy" Proc Natl Acad Sci U S A. 4(1):219-26. 1. Jan. 7, 1997.

Supplementary European Search Report. Application No. 04760621.5 Date of Mailing Apr. 27, 2009.

International Search Report. Application No. PCT/US04/13194 Date of mailing Mar. 18, 2005.

Jaakkola et al. "Transcriptional targeting of adenoviral gene delivery into migrating wound keratinocytes using fire, a growth factor—inducible regulatory element" Gene Therapy 7:1640-1647, (2000).

Palmer et al. "Genetically modified skin fibroblasts persist long after transplantation but gradually inactivate introduced genes" Proc. Nati. Acad. Sci. USA vol. 88, pp. 1330-1334, Cell Biology, Feb. 1991.

Ng et al. "Requirement of an AP—1 site in the Calcium Response Region of the Involucrin Promoter" JBC 275(31): 24080-24088, (2000).

Suzuki et al. "Identification of the hepatocyte mitogen in bovine spleen as heparin-binding growth factors" Biochemical and Biophysical Research Communications vol. 186, Issue 3, pp. 1192-1200, Aug. 14, 1992.

Sato H et al. "Repression of P53-Dependent Sequence-Specific Transactivation by MEF2C" Biochemical and Biophysical Research Communications vol. 214, Issue 2, pp. 468-474, Sep. 14, 1995.

Auerbach et al. "Angiogenesis Induction by Tumors, Embryonic Tissues, and Lymphocyte" Cancer Res; 36:3435-3440, (1976).

Swanson et al. "Characterization of myocyte enhancer factor 2 (MEF2) expression in B and T cells: MEF2C is a B cell-restricted transcription factor in lymphocytes" Molecular Immunology vol. 35, Issue 8, pp. 445-458, May 1, 1998.

Aoki Y et al. "Angiogenesis and hematopoiesis induced by Kaposi's sarcoma-associated herpesvirus-encoded interleukin-6" Blood. 93:4034-4043, (1999).

(56) References Cited

OTHER PUBLICATIONS

Shifren et al. "In the human fetus, vascular endothelial growth factor is expressed in epithelial cells and myocytes, but not vascular endothelium: implications for mode of action" The Journal of Clinical Endocrinology & MetabolismJul. 1, vol. 79 No. 1 316-322, (1994).

Upreti et al. "Preparation of representative homogenates of biological tissues: Effect of salt on protein extraction" Analytical Biochemistry vol. 198, Issue 2, pp. 298-301, Nov. 1, 1991.

Eming et al. "Genetically Modified Human Keratinocytes Overexpressing PDGF-A Enhance the Performance of a Composite Skin Graft" Human Gene Therapy. 9(4): 529-539, Mar. 1998.

Gunther et al. Specific targets in tumor tissue for the delivery of therapeutic genes. Curr Med Chem Anti-cancer Agents 5: 157-171, (2005).

Azimzadeh et al. "Xenograft rejection: molecular mechanisms and therapeutic prospects" Hematology and Cell Therapy . vol. 38, No. 4 ,331-343, (1996).

Gould and Auchincloss. "Direct and indirect recognition: the role of MHC antigens in graft rejection" Immunol Today. 20(2):77-82. Feb. 1999.

Printout from www.hemophilia.org/NhFWeb/MainPgs/MainNHF. aspxmenuid+180&contentid=45, pp. 1-2. printed, Apr. 17, 2012.

Chao et al. "Sustained expression of human factor VIII in mice using a parvovirus-based vector" Blood, vol. 95, No. 5 pp. 1594-1599, Mar. 1, 2000.

Mitrani et al. "Biopump: Autologous skin-derived micro-organ genetically engineered to provide Sustained continuous secretion of therapeutic proteins"Dermatologic Therapy, vol. 24, 489-497, (2011).

International Search Report Application No. PCT/IL2012/050482 Date of Mailing Apr. 2, 2013.

Chen et al.; "Adeno-associated virus mediated interferon-gamma inhibits the progression of hepatic fibrosis in vitro and in vivo", World J. Gastroenterol., 2005, vol. 11, pp. 4045-4051.

Chiou et al.; "Gene Therapy Strategies for the treatment of chronic viral hepatitis", Expert Opinion Biol. Ther., 2001, vol. 1, No. 4, pp. 629-639.

Lippin et al.; "342. Human Erythropoietin Gene Therapy for Patients with Chronic Renal Failure", Molecular Therapy, vol. 11, Supplement 1, May 2005, p. 133.

Elder et al.; "Successful Culture and Seleciton of Cytokine Gene-Modified Human Dermal Fibroblasts for the Biologic Therapy of Patients with Cancer", Human Gene Therapy 7:479-487, Mar. 1, 1996.

Garg et al.; "The Hybrid Cytomegalovirus Enhancer/Chicken β-Actin Promoter along with Woodchuck Hepatitis Virus Post-transcriptional Regulatory Element Enhances the Protective Efficacy of DNA Vaccines", The Journal of Immunology, 2004, pp. 550-558.

Kim et al.; "Lifetime correction of genetic deficiency in mice with a single injection of helper-dependent adenoviral vector", PNAS, vol. 98 No. 23, pp. 13282-13287, Nov. 6, 2001.

* cited by examiner

A

B

A

B

# DERMAL MICRO-ORGANS, METHODS AND APPARATUSES FOR PRODUCING AND USING THE SAME

CROSS REFERENCE TO RELATED APPLICATIONS

This application is a Continuation in Part of U.S. application Ser. No. 13/369,329, filed Feb. 9, 2012, which is a Divisional application of U.S. application Ser. No. 12/216,321 now U.S. Pat. No. 8,142,990, filed Jul. 2, 2008, which is a Continuation of U.S. application Ser. No. 10/834,345, filed Apr. 29, 2004, now U.S. Pat. No. 7,468,242, which claims priority from U.S. Provisional Application No. 60/466,793, filed May 1, 2003, and United to States Provisional Application No. 60/492,754, filed Aug. 6, 2003 and is a Continuation in Part of PCT International Application Numbers PCT/IL02/00877, PCT/IL02/00878, PCT/IL02/00879 and PCT/IL02/00880, all filed Nov. 5, 2002, the disclosures of all of which are incorporated herein by reference in their entirety.

FIELD OF THE INVENTION

The invention relates to the field of tissue based micro-organs, therapeutic tissue based micro-organs and methods and apparatuses for harvesting, processing, implanting and manipulating dermal tissue.

BACKGROUND OF THE INVENTION

Various methods for delivering therapeutic agents are known. For example, therapeutic agents can be delivered orally, transdermally, by inhalation, by injection and by depot with slow release. In each of these cases the method of delivery is limited by the body processes that the agent is subjected to, by the requirement for frequent administration, and limitations on the size of molecules that can be utilized. For some of the methods, the amount of therapeutic agent varies between administrations.

A dermal micro-organ (DMO), which can be sustained outside the body ("ex vivo" or "in vitro") in an autonomously functional state for an extended period of time, and to which various manipulations can be applied, may then be implanted subcutaneously or within the body for the purpose of treating diseases, or disorders, or for plastic surgical purposes. The DMO can be modified to express a gene product of interest. These modified dermal micro-organs are generally referred to as Dermal Therapeutic Micro-Organs (DTMOs).

Skin micro-organs (MO), including layers of epidermal and dermal tissues, for example; as outlined in PCT/IL02/0880, have been observed to be associated with a number of clinical challenges. Harvesting of a skin sample leaves a superficial wound on the patient that may last several weeks and may leave scars. The harvested skin sample requires significant processing to generate micro-organs from this sample. Also, implantation of skin micro-organs subcutaneously or deeper in the body have been found to result in the development of keratin cysts or keratin micro-cysts. Additionally, implantation of skin micro-organs as a graft onto the skin surface in "slits" requires significant technical expertise in order to handle the MO while maintaining its proper orientation.

Harvesting of dermis, e.g., to be used as a "filler material" in a plastic surgical or cosmetic procedure, is known in the art. Conventional harvesting techniques include using a dermatome or scalpel to peel away a layer of epidermis in order to expose a section of dermis. The dermatome or scalpel may then be used again to manually harvest the exposed section of dermis.

Another conventional apparatus for harvesting dermis, albeit not commonly used, is the Martin Dermal Harvester marketed by Padgett (Part No. P-225) for the indication of harvesting dermal cores from the back for subsequent implantation into the lips during cosmetic lip augmentation procedures. To operate this device, which is not commonly used, a sharpened cutting tube, which includes a reusable thick walled tube with an inner diameter of approximately 4.5 mm, is manually rotated at a very slow speed. Using this type of device generally requires applying pressure to the skin surface directly above the harvest site and installing sutures with active tugging as the cutting tube is pushed forward. Furthermore, the resulting harvested dermis is generally not uniform in dimensions and includes "plugs" of epidermis at either end of the dermal core.

SUMMARY OF THE INVENTION

Embodiments of some aspects of the present invention provide a DMO/DTMO with the ability to be maintained ex-vivo in a generally viable state, which may allow various manipulations to be performed on the DMO, while keeping a high production and secretion level of the desired therapeutic agent, as disclosed in United States Application Publication No. US-2012/0201793-A1, which is incorporated herein by reference in its entirety. In addition, embodiments of some aspects of the present invention provide a method of harvesting a DMO and subsequently implanting a DTMO without forming keratin cysts or keratin microcysts, e.g., upon implantation of the DTMO subcutaneously or deeper in the body. Furthermore, it will be appreciated by persons skilled in the art that the methods and devices according to some embodiments of the present invention may be relatively uncomplicated and, therefore, the level of skill required from a professional to carry out the methods and/or to use the devices of the present invention may not be as demanding as those required in conventional procedures.

Some exemplary embodiments of the invention provide a dermal micro-organ (DMO) having a plurality of dermal components, which may include cells of the dermal tissue and a surrounding matrix. The DMO according to embodiments of the invention may generally retain a micro-architecture and three dimensional structure of the dermal organ from which it is obtained and the dimensions of the DMO may allow passive diffusion of adequate nutrients and gases to the cells and diffusion of cellular waste out of the cells so as to minimize cellular toxicity and concomitant death due to insufficient nutrition and accumulation of waste.

In some exemplary embodiments of the invention, the DMO of the invention does not produce keratin or produces negligible amounts of keratin.

In some embodiments of the invention, the DMO does not produce keratin and/or keratin cysts following subcutaneous or deeper implantation in a body.

In another embodiment of the invention, the DMO of the invention produces micro keratin cysts following that will atrophy within a relatively short period of time, e.g., days or weeks after subcutaneous implantation.

In another embodiment of the invention, the DMO contains hair follicles and sebaceous glands.

Further, exemplary embodiments of the invention provide a method and apparatus of harvesting a dermal micro-organ. The method may include stabilizing and/or supporting a skin-related tissue structure from which a dermal micro-organ is to be harvested, e.g., such that the skin-related tissue structure is maintained at a desired shape and/or position, separating at least a DMO from the skin-related tissue structure, and isolating the separated DMO from the body. According to some of these exemplary embodiments, a support structure may include a vacuum chamber able to hold the skin-related tissue structure in a desired shape and position to enable a cutting tool to cut a DMO from the skin-related tissue structure. In one embodiment the support structure includes one or more vacuum channels to fluidically connect the vacuum chamber with at least one vacuum source.

In one embodiment an apparatus for harvesting a dermal micro-organ comprises (a) a support structure to support a skin-related tissue structure from which the DMO is to be harvested, the support structure comprising a first tubular element, and the first tubular element comprising a site of insertion into the apparatus; (b) an introducer; and (c) a cutting tool. In some embodiments, the first tubular element is a guide channel that may guide additional elements, for instance a cutting tool, for insertion into the supported skin-related tissue.

In one embodiment, an apparatus of the invention includes a vacuum chamber further comprising: (a.) two elevated protrusions, a near, i.e., proximal, elevated protrusion and a distal elevated protrusion relative to the site of insertion, wherein the elevated protrusions are able to support a plateau of at least epidermal and dermal skin layers from the skin-related tissue structure above the trajectory of a cutting tool; and (b) a central channel located between the two elevated protrusions, wherein the central channel supports epidermal and dermal skin layers from the skin-related tissue structure so that the dermal skin layer is within the trajectory of a cutting tool when the cutting tool is inserted in the first tubular element of the apparatus.

In another embodiment, an apparatus of the present invention includes an introducer comprises a second tubular element and a fourth tubular element, wherein the second tubular element inserts through the fourth tubular element and extends beyond the distal end of the fourth tubular element and the second and fourth tubular elements together insert at the site of insertion coaxially within the first tubular element; and further, the fourth tubular element remains coaxial and within the first tubular element upon withdrawal of the second tubular element.

In yet another embodiment, an apparatus includes a third tubular element, for instance a cutting tool that inserts within and through the fourth tubular element.

In one embodiment, the cutting tool comprises a coring tube able to cut through the skin-related tissue structure when advance along a cutting axis, wherein the cutting axis is substantially coaxial with the first tubular element. In another embodiment, the coring tube is a rotatable coring tube attached to a power source.

In one embodiment, a vacuum chamber includes a vacuum control mechanism. Implementation of a vacuum condition may for example, include placing a finger over a hole in the vacuum chamber, i.e., a vacuum hole, that when covered creates a vacuum condition. Alternative, release of a vacuum condition, may for example include removal of the finger from over the vacuum hole. In alternate embodiments, any covering or uncovering of the vacuum hole may be used to control vacuum and release conditions, respectfully. In one embodiment, a vacuum control mechanism relies on clamping and unclamping the vacuum line or opening and closing a valve in the vacuum control line.

In one embodiment, a method of harvesting a DMO of the invention includes the steps of: positioning an apparatus at a harvest site in contact with an epidermal surface of a subject; supporting a skin-related tissue structure at the harvest site from which the DMO is to be harvested; puncturing the skin-related tissue structure; cutting the DMO from the supported skin-related tissue structure; and recovering the DMO. In another embodiment, a harvesting method includes making only a single puncture point in the skin-related structure.

In one embodiment, a method of harvesting includes the use of a vacuum to recover the DMO from the coring tube into a closed container. In one embodiment, the closed container is a syringe body. In certain instances, the syringe may have an attached septum. In another embodiment, the DMO remains within the coring tube after retraction from the harvest site and recovering the DMO comprises flushing the DMO from the coring tube.

Further, exemplary embodiments of the invention provide a method of and apparatus for implanting a dermal micro-organ. In one embodiment, the dermal micro-organ to be implanted is a genetically modified dermal micro-organ, which may also be referred to herein as a dermal therapeutic micro-organ (DTMO).

In one embodiment, an apparatus for implanting a DMO or a DTMO includes (a) a loading syringe comprising a first tubular element; (b) an implanting tool comprising a second tubular element; (c) a support structure to hold a skin-related tissue structure in place, wherein the DMO is to be implanted within the skin related tissue structure; (d) an introducer for puncturing the skin at a penetration site; (e) a stopper tool able to be connected to the support structure, the stopper tool comprising a tubular element, and the stopper tool assisting in maintaining the position of a DMO during retraction of the implanting tool.

In an exemplarily embodiment of the invention, a method for implanting a DTMO includes the steps of: (a) loading a DTMO into a loading syringe, the loading syringe comprising a first tubular element; (b) transferring the DTMO from the loading syringe into an implanting tool, the implanting tool comprising a second tubular element; (c) placing an implanting apparatus at an implantation site, wherein the apparatus is in contact with an epidermal layer of the subject and the implanting axis is generally parallel with the epidermal layer; (d) supporting a skin-related tissue structure at the implantation site wherein the DTMO is to be implanted into the skin-related structure; (e) puncturing the skin within the skin-related tissue structure at the penetration site, wherein the skin is punctured using an introducer including an inner needle and an outer sleeve element; (f) removing the inner needle of the introducer and advancing the implanting tool into the skin-related tissue structure along the implanting axis; and (g) withdrawing the second tubular element wherein the DTMO remains within the skin-related tissue structure. In one embodiment, a stopper tool is used to assist in maintaining the position of a DTMO during retraction of the implanting tool. In certain instances, the first and second steps may be optional, as a DTMO may be loaded directly into the distal end of the implantation needle by suctioning from the back end of the needle with a syringe.

In another embodiment, a DTMO may be implanted by directly injecting the DTMO from a syringe through a needle whose distal end is positioned under the skin or at another anatomical location, if linear implantation is not important.

Further exemplary embodiments of the invention provide a genetically modified dermal micro-organ expressing at least one recombinant gene product the DMO having a plurality of dermal components, including cells and matrix of the dermal tissue, which retain the micro-architecture and three dimensional structure of the dermal tissue from which they are obtained, and having dimensions selected so as to allow passive diffusion of adequate nutrients and gases to the cells and diffusion of cellular waste out of the cells so as to minimize cellular toxicity and concomitant death due to insufficient nutrition and accumulation of waste, wherein at least some of the cells of the DMO express at least one recombinant gene product or at least a portion of the at least one recombinant gene product, as described in United States Publication No. US-2012-0201793-A1, and incorporated herein in full. In still other exemplary embodiments, the at least one recombinant gene product is an at least one recombinant protein.

In some embodiments of the invention, the genetically modified DMO of the invention produces substantially no keratin.

In some embodiments, the invention provides a method of delivering to a recipient a recombinant gene product produced by the DMO.

In some embodiments, the invention provides a method of inducing a local or systemic physiological effect by implanting a DMO in a recipient.

In another embodiment the invention provides a method of delivering a protein of interest to a subject. The method includes implanting the genetically modified DMO into the skin, under the skin or at other locations in the body.

In another embodiment, the invention provides a method of implanting a DTMO so as to avoid or to reduce keratin cyst formation.

In one embodiment, the invention provides a method for removal of an implanted DTMO.

BRIEF DESCRIPTION OF THE DRAWINGS

Non-limiting embodiments of the invention are described in the following description, to be read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale.

FIG. 5A is a schematic illustration of a lateral view of embodiments of a harvesting apparatus. FIG. 5B is a schematic illustration of a cross-sectional view of the apparatus of FIG. 5A externally supporting a skin-related tissue structure from which a dermal micro-organ may be harvested at a desired position;

FIG. 10A shows a syringe with a septum and collet inserted through a support structure guide channel and an outer sleeve, wherein the support structure is connected to a vacuum source. FIG. 10B shows an embodiment of a syringe with a collet and needless valve attached to the back end of a coring needle. The T-end of an introducer (1008) is identified for orientation purposes;

Figure 1:
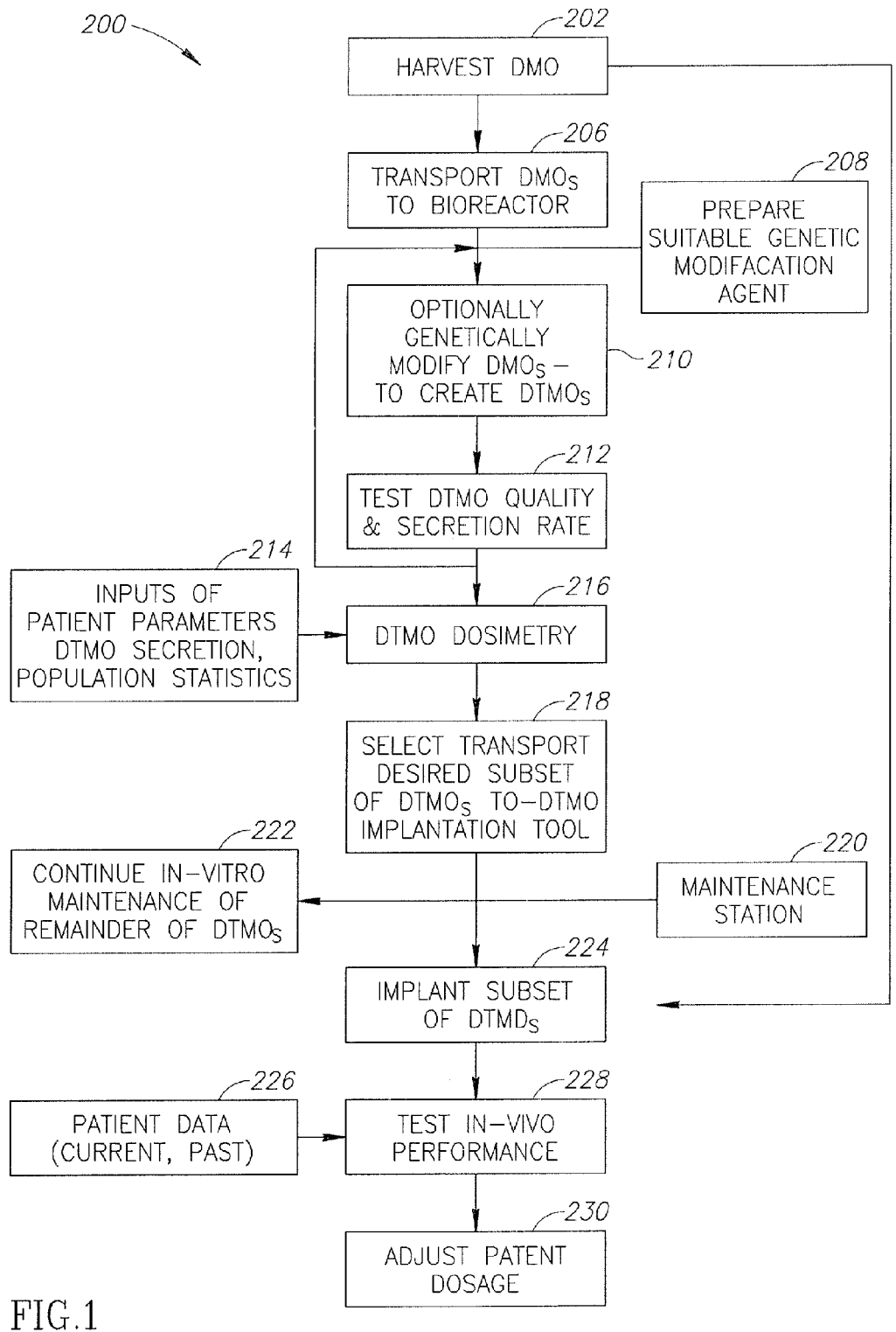
FIG. 1 is a schematic block diagram of an exemplary method of producing and utilizing dermal therapeutic micro-organs (DTMOs), in accordance with an exemplary embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention. In still other instances, methods, procedures and components described in United States Publication No. US-2012/0201793-A1 are incorporated herein by reference in their entirety.

I. Exemplary Definitions of Terms Used Herein

The term "explant" as used herein, refers in some embodiments of the invention, to a removed section of living tissue or organ from one or more tissues or organs of a subject, wherein an "explant" may for example be a dermal micro-organ.

The term "dermal micro-organ" or "DMO" as used herein, refers in some embodiments of the invention, to an isolated tissue or organ structure derived from or identical to an explant that has been prepared in a manner conducive to cell viability and function, while maintaining at least some in vivo interactions similar to the tissues or organ from which it is obtained. DMOs may include plurality of dermal components that retain the micro-architecture of the tissue or organ from which they were derived, and three dimensional structure of the dermal tissue from which they are derived, having dimensions selected so as to allow passive diffusion of adequate nutrients and gases to cells within the DMO and diffusion of cellular waste out of the cells of the DMO so as to minimize cellular toxicity and concomitant death due to insufficient nutrition and accumulation of waste. DMOs may consist essentially of a plurality of dermis components (tissue components of the skin located below the epidermis). These components may contain skin fibroblast, epithelial cells, other cell types, bases of hair follicles, nerve endings, sweat and sebaceous glands, and blood and lymph vessels. Wherever used herein below, the description of the embodiments related to DMO relates also to a MO. Further, whenever the term "dermal tissue" is used, it also relates to "dermal organ" and a DMO.

As used herein, the term "microarchitecture" refers, in some embodiments of the invention, to the characteristic of the explant in which, in one embodiment at least about 50%, in another embodiment, at least about 60%, in another embodiment at least about 70%, in another embodiment, at least about 80%, and in another embodiment, at least about 90% or more of the cells of the population, maintain, in vitro, their physical and/or functional contact with at least one cell or non-cellular substance with which they were in physical and/or functional contact in vivo. Preferably, the cells of the explant maintain at least one biological activity of the organ or tissue from which they are isolated.

The term "donor" as used herein, refers in some embodiments of the invention to a subject, from which the explant is removed and used to form, or which is already in the form of, one or more micro-organs. In one embodiment, the donor is a human subject. In another embodiment, the donor is a non-human mammalian subject.

The term "therapeutic micro-organ (TMO)" as used herein, refers in some embodiments of the invention to a dermal micro-organ (DMO) that can be used to facilitate a therapeutic objective, such as, for example, an DMO that has been genetically altered or modified to produce a therapeutic agent, such as a protein or an RNA molecule. The therapeutic agent may or may not be a naturally occurring body substance. Wherever used hereinbelow, the description of the embodiments related to TMO relates also to DTMO which is a therapeutic Dermal MO which may be in some embodiments of the invention genetically modified.

The term "implantation" as used herein, refers in some embodiments of the invention, to introduction of one or more TMOs or DTMOs into a recipient, wherein said TMOs or DTMOs may be derived from tissues of the recipient or from tissues of another individual or animal. The TMOs or DTMOs can be implanted in a slit within the skin, can be subcutaneously implanted, or may be implanted by placement at other desired sites within the recipient body. In one embodiment, a DTMO is derived from tissue of the recipient. In one embodiment, a DTMO is implanted substantially into the dermal layer of skin tissue. In one embodiment, a DTMO is implanted between the dermal and fat layer of skin tissue.

The term "recipient" as used herein refers, in some embodiments of the invention, to a subject into which one or more TMOs or DTMOs are implanted. In one embodiment, the recipient is a human subject. In another embodiment, the recipient is a non-human mammalian subject. In some embodiments, a recipient receives one or more autologous TMOs or DTMO.

The term "in vitro" as used herein should be understood to include "ex-vivo".

The term "coring tube" as used herein may relate, individually or collectively, to the terms "cutting tool", "cutting tube" and "coring needle", "coring tool", as well as to any other elements with similar functionalities. In some embodiments, a coring needle of this invention is for single use.

The term "implanting tool" as used herein may relate, individually or collectively, to the terms "implantation needle", "implanting needle" and "implanting tube", as well as to any other elements with similar functionalities. In some embodiments, an implanting tool of this invention is for single use.

The term "tubular element" as used herein refers to an element having the form of or consisting of a tube, wherein a tube refers to any of various usually cylindrical structures or devices. In one embodiment, a tubular element is an element having the form of a hollow elongated cylinder. In another embodiment, a tubular element is an element having the form of a cylindrical channel, e.g., a tunnel or channel cut through a solid mass. In yet another embodiment, a tubular element is open at both ends. In still another embodiment, a tubular element is open at one end. In a further embodiment, a tubular element comprises a beveled needle tip at one end. In another embodiment, a tubular element comprises at least one blunt end that is sharpened. In one embodiment a tubular element is an element having the form of a solid, non-hollow elongated cylinder, for instance a rod. In one embodiment, a tubular element may include a guide channel.

The term "rod" as used herein refers to a straight three-dimensional element, which has a solid geometry. In one embodiment, the rod has a circular cross section. In one embodiment, the rod has a non-circular cross-section.

The term "skin-related tissue structure", as used herein, refers to a structure of tissue components that may be stabilized and/or supported by apparatuses defined herein to enable the harvesting of a dermal micro-organ therefrom or for the implantation of a DMO therein. A skin-related tissue structure may include components of the epidermal tissue, and components of the dermal tissue. Optionally, the skin-related tissue structure may include fat tissue and/or muscle tissue in the vicinity of the dermal tissue.

In one embodiment, a skin-related tissue structure of the present invention includes the skin tissue components drawn into the central channel under vacuum conditions. In one embodiment, a skin-related structure includes epidermal, dermal and fat tissue. In another embodiment, a skin-related structure includes epidermal, dermal, fat and muscle tissue.

The term "central channel" as used herein may in some embodiments of the invention be used interchangeable with the term "vacuum chamber".

The term "coaxial", as used herein, refers to a radial symmetry of concentrically or approximately concentrically positioned components. In this way, tubular elements may be positions approximately equidistant from a common axis. In one embodiment, a cutting tool is aligned approximately equidistant from a common axis presented by a guide channel. In one embodiment, a cutting tool is aligned approximately equidistant from a common axis presented by a central channel.

As used herein, the term "approximately" refers to a range of values within plus or minus 10% of an ideal. For example, approximately coaxial tubular elements may share the identical central axis or may be have central axes that are within 10% of a shared identical central axis.

In one embodiment, one tubular element is contained within another tubular element, but the central axis of both tubes need not be aligned.

While, for clarity and completeness of presentation, all aspects of the production to and utilization of DTMOs are described in this document, and embodiments of the invention are described from the start of the processes to their ends, it should be understood that each of the aspects described herein can be used with other methodologies and/or equipment for the carrying out of other aspects and can be used for other purposes, some of which are described herein. The present invention includes portions devoted to the preparation and maintenance of dermal micro-organs for transformation into DTMOs. It should be understood that the dermal micro-organs produced according to these aspects of the invention can be used for purposes other than for transformation into DTMOs In some embodiments of the invention, the micro-organ is a DMO including a plurality of dermis components, for example, fibroblasts and/or epithelial components containing nerve endings and/or sweat glands and/or sebaceous glands and/or blood and lymph vessels and/or elastin fibers and/or collagen fibers and/or endothelial components and/or immune system derived cells and/or extra-cellular matrix. Conventional subcutaneous implantation of a micro-organ including epidermal layers ("split thickness skin MO") in mice and pigs, may result in formation of keratin cysts or macro-keratin cysts. In contrast, when skin tissue is sampled to obtain a DMO or when a DMO is directly harvested, according to exemplary embodiments of the invention, after subcutaneous implantation or implantation in other anatomical locations, no cysts or macro cysts are observed in mice, pigs or in humans. It should be noted that the biological activity (for example, secretion of a therapeutic protein, e.g., erythropoietin and elevation of hematocrit as a result) of a DTMO according to embodiments of the invention may be comparable to or even higher than split thickness skin derived TMO.

In general, production of DTMOs may include DMO harvesting, maintaining the DMO and/or modifying the DMO and/or genetically altering them and, in some embodiments, verifying the production of a desired agent (for example proteins) by the DMO. Utilization of the DTMO may include production, within a patient's or animal's own body, of therapeutic substance, such as proteins, for treatment of a subject. For example, the DTMO can be implanted into or under the skin or within the body of the subject to produce the agent/protein in vivo.

In one embodiment, a DTMO is not encapsulated in an immunoprotective capsule or sheath.

In some embodiments of the invention, the DMO may contain tissue of a basal epidermal layer and, optionally, other epidermal layers of the skin. In other embodiments, the dermal micro-organ does not include basal epidermal layer tissue.

In some embodiments of the invention, the DMO does not include epidermal layers. In other embodiments, the DMO may contain a few layers of epidermal tissue. In some embodiments, the dermal micro-organ may lack a complete epidermal layer. In certain instances, a DMO may include invaginations of the epidermis within the dermal tissue layers, while still lacking a complete epidermal layer.

In one embodiment of the invention, the DMO includes the entire cross-section of the dermis. In another embodiment of the invention, the dermal micro-organ includes part of the cross-section of the dermis. In a further embodiment, the DMO includes most of the cross section of the dermis, namely, most of the layers and components of the dermis including the papillary and reticular dermis. In a further embodiment, the DMO includes primarily dermal tissue, but may also include fat tissue. In some embodiments of the invention, the DMO does not produce keratin or produces a negligible amount of keratin, thereby preventing the formation of keratin cysts following implantation in a recipient.

II. Methods and Apparatuses for Harvesting a DMO

The DMO to be harvested can be removed from the body by any means of removing tissue known in the art, such as biopsy procedures. The harvesting procedure keeps intact the micro-architecture of the tissue from which it is removed. In one embodiment the DMO may be obtained by direct biopsy and then be cut to the required size. In another embodiment, a tissue sample may be obtained by direct biopsy, in which the desired size of the dermal micro-organ is obtained. In another embodiment, non-desired tissue may be cut from the harvested biopsy or directly harvested micro-organ. In one embodiment, a DMO may be obtained by direct biopsy and then processed to become a DTMO by genetic modification of the DMO in vitro. In one embodiment a DMO or a DTMO may be labeled in vitro for identification purposes, e.g., a DMO or a DTMO may be colored prior to implantation by an inert, biocompatible ink or stain containing, for example, a chromophore, which may be visible to the naked eye or may require special illumination conditions to visualize it.

In some embodiments of the invention, the dermal micro-organ is directly harvested from the body. In other embodiments, a dermal micro-organ is harvested with the aid of a harvesting apparatus. The inner diameter dimension of a cutting tool used to harvest a dermal micro-organ may be, for example, about 0.5-4 mm. In another embodiment, the dimension may be, for example, 1.71 mm. In yet another embodiment, the dimension may be 1.21 mm. In still another embodiment, the dimension may be, for example, 1-3 mm. In a further embodiment, the dimension may be, for example, 2-4 mm. In one embodiment the dimension may be, for example, 1-2 mm. In another embodiment, the dimension may be 0.5-1.5 mm. In yet another embodiment, the dimension may be, for example, about 1.5 mm. In still another embodiment, the dimension may be, for example, about 2 mm.

In some embodiments, the cutting tool has dimensions corresponding to needle size dimensions. In one embodiment, the cutting tool is, for example, a 14 GA needle. In another embodiment, the cutting tool is a 15 GA needle. In yet another embodiment, the cutting tool is a 16 GA needle. In yet another embodiment, the cutting tool is a 17 GA needle. In still another embodiment, the cutting tool is an 18 GA needle. In a further embodiment, the cutting tool is a 19 GA needle. In one embodiment, the cutting tool is a 12 GA needle. In another embodiment, the cutting tool is a 13 GA needle. The wall thickness of a cutting tool corresponding to a needle size dimension, may be for example a regular wall thickness (RW), a thin wall thickness (TW), a extra thin wall thickness (XTW), or any thickness known in the art.

The shape of the tip of a cutting tool may also play a role in harvesting a DMO. A sharp tip may be used, as is, e.g., commercially available needles. Alternatively, a cutting tool may have a tip, which has been sharpened, e.g., by polishing or through the use of chemical treatments or using electrochemical erosion. In one embodiment, the sharp tip of a cutting tool is symmetrical sharpened. The sharpening of the tip may be either on the OD surface or the ID surface. For example, the tip may be sharpened by removing material from the outer or inner surface of the tip.

In some embodiments, the harvested DMO may not retain its cylindrical shape after harvesting, i.e., at least one dimension of its cross section may expand while at least another dimension of its cross section may contract. In one embodiment, for example, at least one dimension may be 0.5-3.5 mm and at least one dimension may be 1.5-10 mm.

In another embodiment, the dimensions of the tissue being harvested may be, for example, about 5-100 mm in length. In another embodiment, the dimensions of the tissue being harvested may be, for example, about 10-60 mm in length. In another embodiment, the dimensions of the tissue being harvested may be, for example, about 20-60 mm in length. In another embodiment, the dimensions of the tissue being harvested may be, for example, about 20-50 mm in length. In another embodiment, the dimensions of the tissue being harvested may be, for example, about 20-40 mm in length. In another embodiment, the dimensions of the tissue being harvested may be, for example, about 20-100 mm in length. In another embodiment, the dimensions of the tissue being harvested may be, for example, about 30-100 mm in length. In another embodiment, the dimensions of the tissue being harvested may be, for example, about 40-100 mm in length. In another embodiment, the dimensions of the tissue being harvested may be, for example, about 50-100 mm in length. In another embodiment, the dimensions of the tissue being harvested may be, for example, about 60-100 mm in length. In another embodiment, the dimensions of the tissue being harvested may be, for example, about 70-100 mm in length. In another embodiment, the dimensions of the tissue being harvested may be, for example, about 80-100 mm in length. In another embodiment, the dimensions of the tissue being harvested may be, for example, about 90-100 mm in length. In another embodiment the length may be around 20 mm. In another embodiment, the length may be about 30 mm. In another embodiment, the length may be about 40 mm.

When a DMO has the above listed dimensions, it maybe maintained in vitro, e.g., in a growth medium under proper tissue culture conditions for extended periods of time, for example, several days, several weeks or several months. The DMO may be maintained, for example, in-vitro in defined growth media. In one exemplary embodiment the growth media may include growth factors, fetal calf serum (FCS), human serum, or Synthetic Serum Substitute (SSS). In another exemplary embodiment the growth media may include serum either from the donor or the recipient subject. In yet another embodiment the growth media may include autologous serum. In another embodiment, no serum is added to the media.

In accordance with an aspect of some embodiments of the invention, only a portion of a DTMO generated may be used in a given treatment session. The remaining DTMO tissue may be returned for maintenance and/or may be stored (e.g., cryogenically or otherwise) for later use. In one embodiment, a DMO is stored, for example cryogenically or otherwise, prior to genetic modification processing. In another embodiment, a DMO is stored, for example cryogenically or otherwise, following genetic modification processing.

It is a feature of some embodiments of the invention that a large number of dermal micro-organs may be processed together in a batch process into DTMOs, as described below. This may allow for more convenient processing, but will not allow for determination of the secretion level of each DTMO separately. In other embodiments, a DMO may be processed independently into a DTMO, as described herein.

In some exemplary embodiments of the invention a potency assay may be performed for the therapeutic agent, which may be produced and/or secreted by either a single DTMO or a batch of DTMOs. The potency assay may include, for example, a cell proliferation assay in which the proliferation response of the cells is mainly dependent on the presence of the therapeutic agent in the growth media of the cells. In one embodiment, analysis of a DTMO may use for example an ELISA assay in order to quantify secretion levels of an at least one secreted therapeutic agent.

According to some embodiments of the invention, a method of harvesting the DMO may include stabilizing and supporting a skin-related tissue structure from which a DMO is to be harvested, e.g., such that at least the DMO and/or one or more other tissue segments in its vicinity are maintained at a desired shape and/or position, separating at least a portion of the DMO from surrounding tissue, and extracting the separated DMO, as described in detail below.

FIG. 1 shows an overview of a methodology for producing and utilizing DMOs and DTMOs, in block diagram form, in accordance with an exemplary embodiment of the invention. Similarly, a DTMO may be produced by following the steps described independent of a bioreactor. At block 202 a DMO is harvested from a subject. In some embodiments of the invention, the DMO is harvested from the same subject to which therapy will later be applied. In an embodiment of the invention, the DMO is from dermal tissue. Optionally, other tissues are harvested and used in a manner similar to that described below with reference to dermal tissue. While the method described below is exemplary, other methods of harvesting tissue samples can be used in some embodiments of the invention. If desired, the DMO or DTMO can be cryogenically stored for later use (i.e., introduction at the same stage of the process). Alternatively, for certain embodiments, the DMO can be implanted directly back into the patient from which it was harvested to produce a therapeutic, cosmetic, or other physiological affect.

In order for a DMO to be a viable micro-organ, it must have at least one dimension that is small enough that nutrients can diffuse to all the cells of the DMO from a nutrient medium which contacts the DMO and that waste products can diffuse out of the DMO and into the medium. This enables the DMO to be viable in vitro long enough for the further processing described below and for the optional further utilization of the DMO as a source for a therapeutic agent, such as a protein. The method of harvesting a DMO generally results in a DMO having an in vitro life of several months.

A suitable genetic modification agent is prepared (block 208). Alternative exemplary methods of preparing the agent include creation of aliquots with a desired amount of a modifying agent using a predefined dilution buffer containing modifying agent, such as for example a viral vector, and validating the activity of the modifying agent. All of these processes are well known in the art. At this point the DMO can be stored cryogenically, for later introduction at the same place in the process. This can be performed using known protocols for gradual freezing of tissues and cells, using for example, DMEM medium containing 10% DMSO At block 210 the DMO is genetically altered. As described above, many methods of genetic alteration are known and may be used in conjunction with the present invention. As an example, the following description is based on using a viral vector to insert a gene into the cells of the DMO. This process is well known and will not be further described, except as to the particular methodology and apparatus for introducing the virus to the DMO.

At block 212 the genetically altered DTMO is optionally tested for production and secretion rates of the therapeutic agent. There are various methods of determining the quantity of secretion, for example, ELISA, other immunoassays, spectral analysis, etc. In addition the quality of the secretion is optionally tested, for example for sterility and/or activity of the secreted protein. This may be performed periodically or continuously on-line. At this point the DTMO can be cryogenically stored for later use.

At blocks 214 and 216, the amount of DTMO required for producing a desired therapeutic effect is determined. As indicated below, the therapeutic dose requirements can be estimated from measured secretion rates, patient parameters and population statistics on the estimated or known relationship between in vitro secretion and in vivo serum levels.

At block 218 the desired number of the DTMOs are selected. A DTMO is loaded into an implantation tool. Exemplary implementation tools are described below.

If the DTMOs must be transported prior to being transferred to the implantation tools, it is optionally held (220) in a maintenance station or under maintenance conditions, in which the temperature, humidity, etc. are held at levels that allow the DTMO to stay viable during transport. The remaining DTMOs are optionally maintained in vitro for future use. This can be at warm incubator conditions (30-37° C.), in conditions as described above at cool incubator conditions (4° C.), which may prolong its viability in vitro, or under cryogenic conditions.

At block 224, a subset of the DTMOs is implanted into the subject. An exemplary embodiment of a method of implantation is described below. Other methods of doing so will occur to persons of skill in the art and are primarily dependent on the specific geometry of the micro-organ being used. Animal studies have shown that the DMOs and DTMOs remain viable in vivo, in the sense that the DTMO continues to produce and secrete the therapeutic agent for a period of weeks and months following implantation. In animal studies, therapeutic amounts are produced for periods up to 160 days (or longer). While the tissue of the DMO or DTMO appears to be integrated or well taken into the tissue of the subject into which it is implanted (especially if the tissue is implanted in a tissue of the same kind from which it was harvested), the cells included within the DMO or the DTMO continue to produce and secrete the therapeutic agent.

The in vivo performance of the DTMO is optionally determined (block 228). Based on this evaluation for example, and/or on past patient data (block 226), patient dosage may then be adjusted (block 230) by increasing the amount of the implant or removing some of the implant, as described below. As the efficacy of the implant changes, additional DTMOs can be implanted.

Genetic alteration may generally include genetically engineering a selected gene or genes into cells that causes the cells to produce and optionally to secrete a desired therapeutic agent such as a protein. In an embodiment of the invention, at least part of the process of sustaining the DMO during the genetic alteration, as well as the genetic alteration itself, may be performed in a bioreactor.

According to some exemplary embodiments of the invention, a method of harvesting a DMO from a subject may include generating and/or maintaining a skin-related tissue structure associated with the DMO, e.g., located generally at a targeted harvest site for harvesting the DMO, at a desired shape and position such that the cutting tool may be able to separate the DMO from tissue in the vicinity of the DMO. For example, an epidermis portion in the vicinity of the targeted harvest site may be lifted, e.g., by attaching at least part of the epidermis portion to a predefined surface such that at least part of the skin-related tissue structure may be lifted and maintained at the desired shape and/or position. According to some exemplary embodiments, attaching the epidermis to the predefined surface may include applying a vacuum condition, e.g., as described below. Alternatively or additionally, attaching the epidermis to the predefined surface may include applying an adhesive to the surface.

Figure 2:
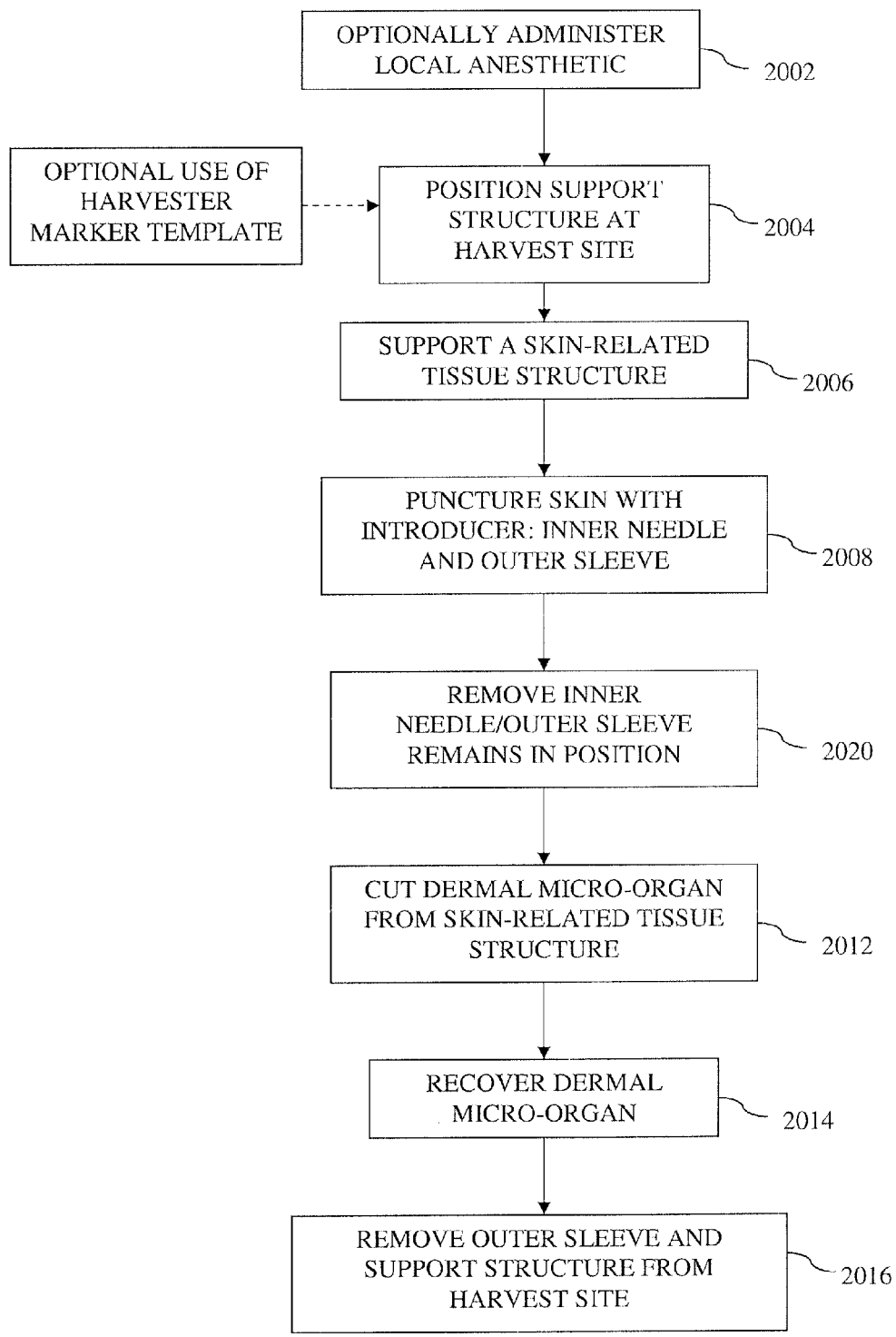
FIG. 2 is a schematic flowchart illustrating a method of harvesting a DMO according to some exemplary embodiments of the invention.

Reference is now made to FIG. 2, which schematically illustrates a flowchart of a method of harvesting a DMO according to some exemplary embodiments of the invention, and to FIGS. 3A-3G, which schematically illustrate exemplary stages of harvesting a DMO 3024 located within a skin-related tissue structure.

As indicated at block 2002, the method may optionally include locally administering an anesthetic, e.g., as is known in the art, to the vicinity of the DMO to be harvested.

Use of DTMOs for protein or RNA based therapy may, in certain circumstances, necessitate use of multiple DTMOs. As described throughout, DMOs and DTMOs may be maintained in vitro for extended time periods or stored cryogenically or otherwise, for later use. Therefore, in some instances, multiple DMOs may be harvested consecutively during a single procedural time period from the same subject. In this way, multiple DMOs may be harvested from the subject for later use, without the subject undergoing separate harvesting procedures on separate days for each DMO needed. In one embodiment, a harvester marker template may be used prior to positioning a harvester apparatus on a subject's epidermal surface (step 2004), in order to mark multiple sites for harvesting. In one embodiment, a harvester marker template is positioned on the epidermal surface of a subject, and the epidermal surface is then marked to indicate, for example, area for application of local anesthesia, alignment lines and harvesting lines. In one embodiment, the surface is marked using a surgical pen or marker. In one embodiment, the surface is marked using a non-permanent dye or ink.

Figure 4:
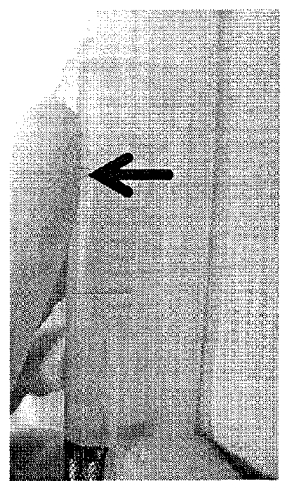
FIGS. 4A-4E show embodiments of some elements of a harvesting apparatus, a medical drill for use with a harvesting apparatus and a syringe, septum and collet for use to harvesting the DTMO. 4A shows an embodiment of a syringe (4002) for harvesting and a septum (4004). 4B shows an embodiment of a collet. 4C shows an embodiment of a support structure with a vacuum hole being covered by a finger. 4D shows an embodiment of an introducer: inner needle (4006—needle) and outer guide (4008—white sleeve). 4E shows an embodiment of a cutting tube (4010), a drill (4012) and a drill hand piece (4014).
Figure 4:
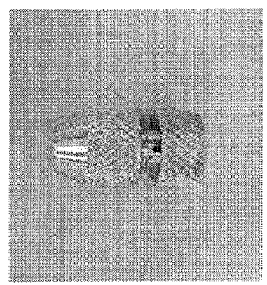
Figure 4:
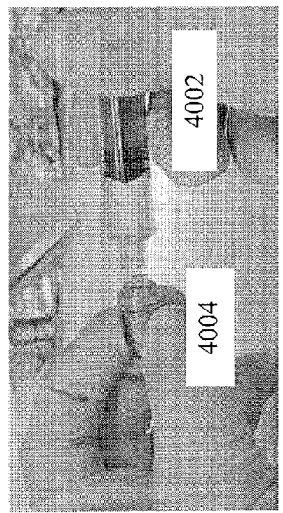
Figure 4:
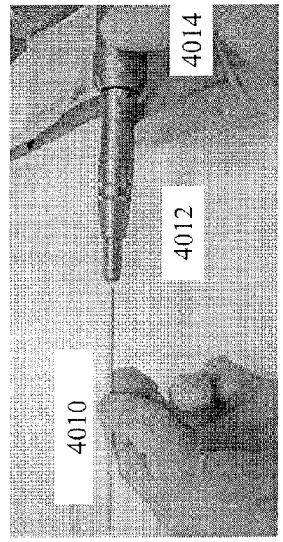
Figure 4:
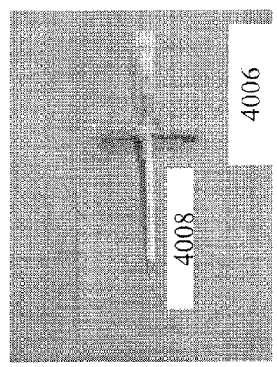
Figure 5A:
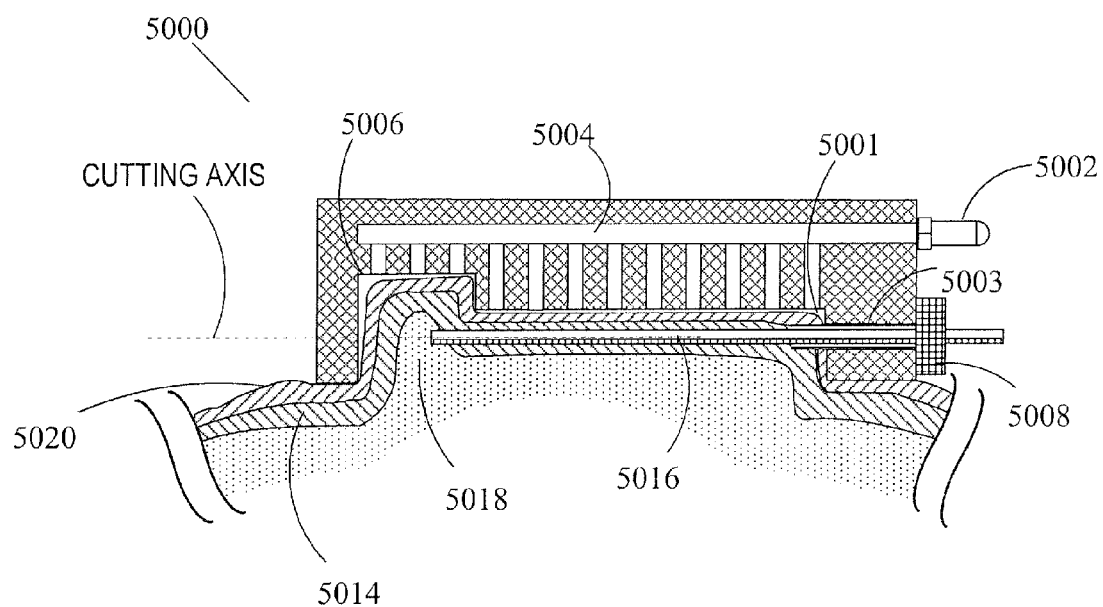
FIG. 5A-B are schematic illustration of some components of a dermal harvesting apparatus according to another exemplary embodiment of the invention.
Figure 6:
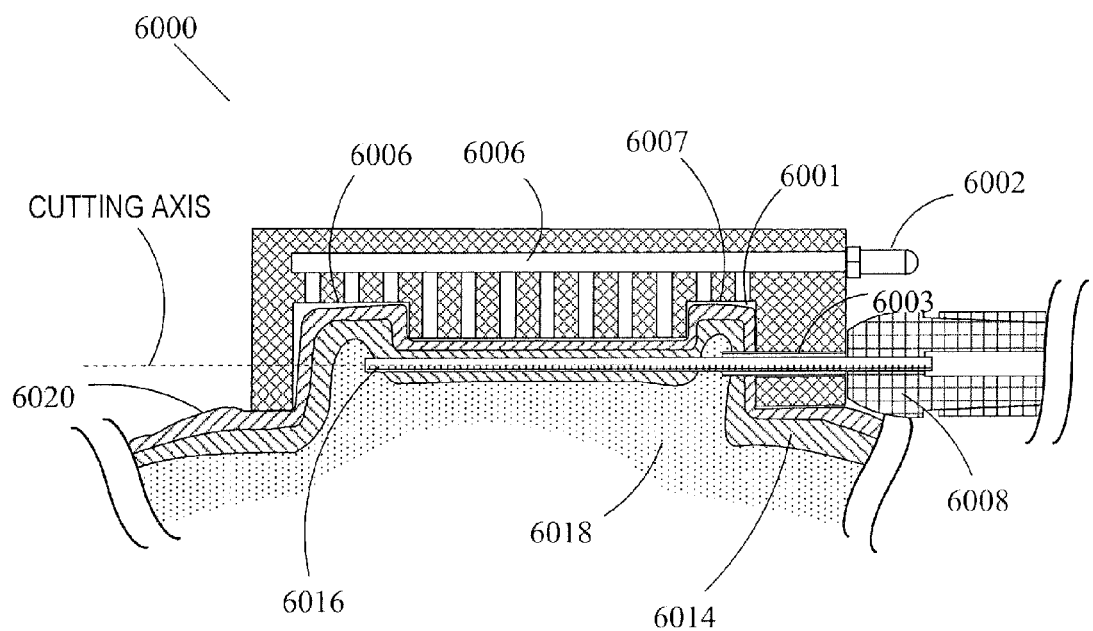
FIG. 6 is a schematic illustration of some components of a dermal harvesting apparatus according to yet another exemplary embodiment of the invention.
Figure 11:
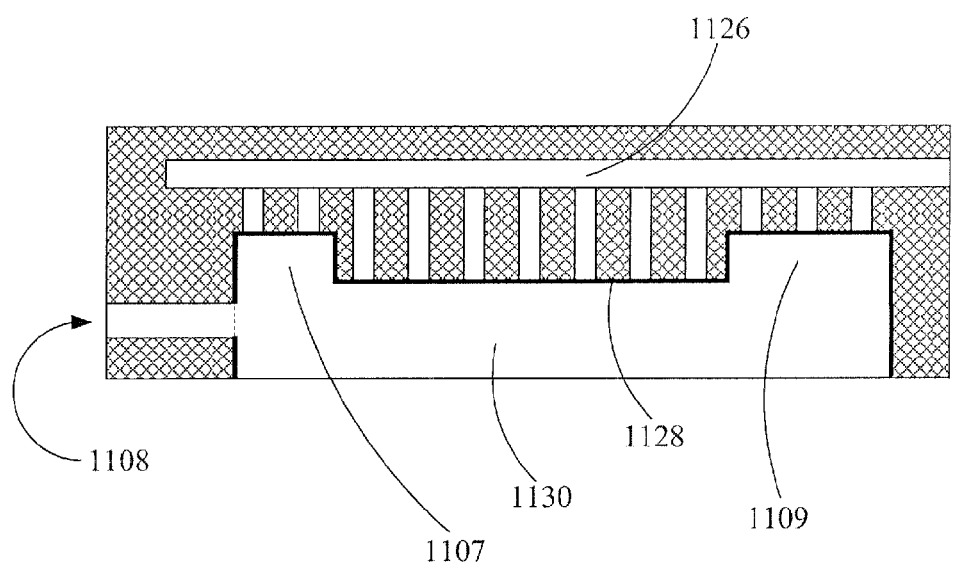
FIG. 11 shows a schematic illustration of an embodiment of a support structure.

As indicated at block 2004, the method may further include positioning an apparatus including a support structure, (e.g., FIG. 4C; FIG. 5A; FIG. 6; FIG. 11), at a given harvest site so that the support structure, or a portion thereof, is in contact with an epidermal surface of the subject. In some embodiments, a contact between a support structure of this invention and the epidermal surface of a subject must be air-tight so that a vacuum seal may be formed at a later step. In one embodiment, a harvest site is on a subject's back. In another embodiment, a harvest site is on a subject's abdomen. In yet another embodiment, a harvest site may be at another location on a subject's body.

Figure 3A:
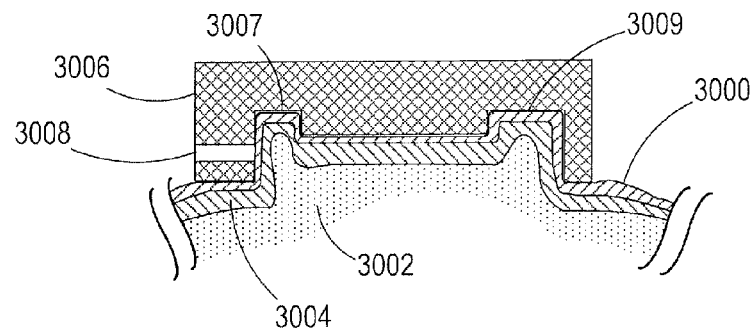
FIGS. 3A-3G are schematic illustrations of exemplary stages of harvesting a DMO in accordance with a method of FIG. 2.
Figure 13:
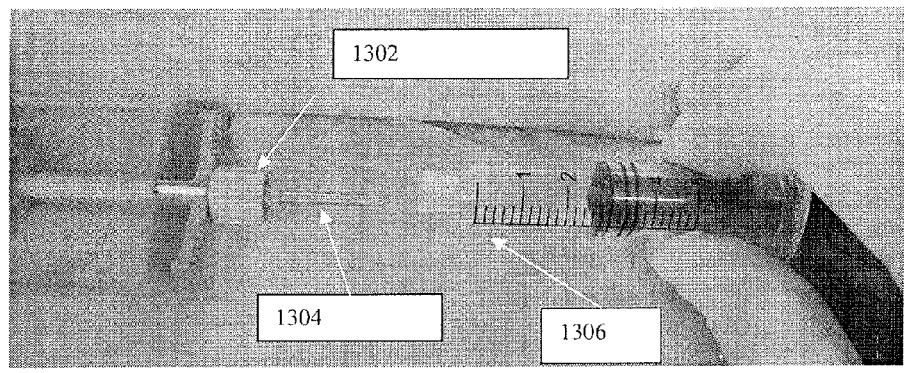
FIG. 13 shows an embodiment of a syringe (1306) being attached to a glued-on male luercap (1302) near the back end of a coring needle (1304)

As indicated at block 2006 and FIG. 3A, a support structure (e.g., FIG. 4C; FIG. 13A; FIG. 6; FIG. 11), which may include a vacuum chamber (FIG. 11 1130) and guide channel 2008 (FIG. 11 1108), under vacuum conditions may be used to hold and support the skin-related tissue structure including epidermal (3000), dermal (3002) and fat (3004) tissue layers, in place for proper harvesting of a DMO. For example, application of vacuum conditions causes a vacuum to be formed within the vacuum chamber thereby drawing the epidermal surface of the skin-related structure into the interior of the support structure, wherein a central channel may support epidermal and dermal skin layers of the skin-related structure.

As used herein, the term "guide channel" may also be referred to herein as a "needle guide channel".

Under vacuum conditions a central channel may provide support for the skin-related tissue structure to be shaped so that dermal tissue is within the central channel. In some exemplary embodiments, the vacuum chamber includes one elevated protrusion. In other exemplary embodiments, the vacuum chamber includes two elevated protrusions. In instances where a support structure that includes one or two elevated protrusions is used, the elevated protrusions additionally may support epidermal and dermal skin layers of the skin-related structure.

In certain instances, application of vacuum conditions using a vacuum chamber with two elevated protrusions may create a precise geometry of the skin-related structure such that dermal tissue is harvested and a plug of epidermal tissue is not harvested.

In exemplary embodiments, a vacuum condition may cause the skin-related structure to be held at an inner support surface of the vacuum chamber, including within a central channel and elevated protrusions if present. The guide channel 3008, which in one embodiment may be tubular in shape, may provide guidance and/or stability for inserting and/or using a cutting tool to ensure proper cutting along a cutting axis. In some embodiments, the cutting axis is coaxial with the guide channel. While the coring tube is coaxial with the guide channel, the coring needle may not always be in the vertical center of the central channel. In one embodiment, the coring tube is in the horizontal center of the central channel.

In certain embodiments, the inner dimensions of a support structure including a vacuum chamber may be between 3.0-8.0 mm. In one embodiment, the dimension may be, for example 3.0 mm in diameter. In another embodiment, the dimension may be, for example 3.5 mm in diameter. In a yet another embodiment, the dimension may be, for example 4.0 mm in diameter. In another embodiment, the dimension may be, for example 4.5 mm in diameter. In another embodiment, the dimension may be, for example 5.0 mm in diameter. In still another embodiment, the dimension may be, for example 5.5 mm in diameter. In yet another embodiment, the dimension may be, for example 6.0 mm in diameter. In a further embodiment, the dimension may be, for example 6.5 mm in diameter. In another embodiment, the dimension may be, for example 7.0 mm in diameter. In yet another embodiment, the dimension may be, for example 7.5 mm in diameter. In another embodiment, the dimension may be, for example 8.0 mm in diameter.

In one embodiment, the appropriate sized support structure having particular inner dimensions of a vacuum chamber is pre-determined prior to actual harvesting.

Figure 3B:
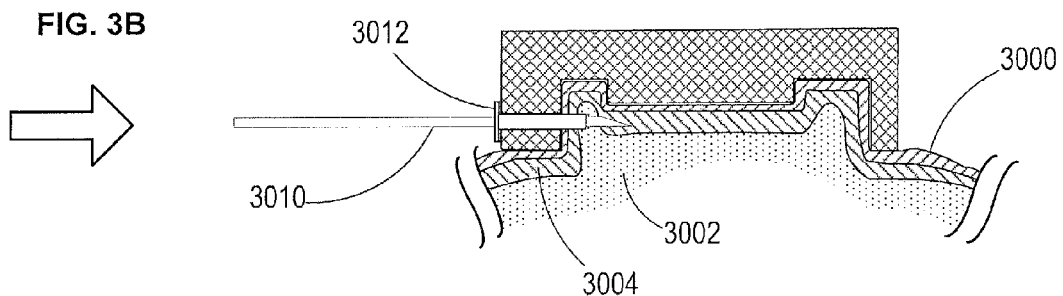

As indicated at block 2008 and FIG. 3B, an introducer (e.g., FIG. 4D), including for instance, an inner needle (3010; 4006) and an outer sleeve (3012; 4008), may then be used to puncture the skin-related tissue by inserting the introducer through the guide channel of the support structure, 3006, and into the skin-related tissue structure at a point of penetration. This single puncture site may be used for all further entry and egress into and out of the skin-related structure. In this way damage and scarring to the subject is limited. Introduction of the cutting tool through the outer sleeve of the introducer prevents or minimizes harvesting of epidermal tissue.

An introducer may be composed of tubular elements, for instance an inner needle and an outer sleeve. In some embodiments, the outer sleeve is fitted over the inner needle. Together they may be inserted into the skin-related structure. In certain embodiments, where a support structure with a vacuum chamber including a proximal elevated protrusion is used the configuration of the skin-related tissue is such that insertion of the introducer is generally perpendicular to the skin surface at the point of penetration. In one embodiment where a support structure with a vacuum chamber including a proximal elevated protrusion is used, an introducer may be inserted into the skin-related structure such that the tip of the inner needle extends into the region of tissue in the area of the first, i.e., proximal elevated protrusion, 3007, and the distal end of the outer sleeve extends to about mid-way under this first elevated protrusion. In one embodiment, following insertion of the introducer, the distal end of the outer sleeve transverses all of the layers of the skin at the puncture site and is located in the underlying fat layer.

In the absences of the step at block 2008, using an introducer to puncture the skin, the step at block 2012 below would result in the harvesting of a plug of full thickness skin prior to the harvest of the dermal micro-organ, which would necessitate additional processing of the tissue to remove the full thickness skin plug in order to produce a DMO.

In one embodiment, the inner needle is beveled. In another embodiment, the inner needle is not beveled. In one embodiment, insertion of the introducer is with the bevel of the inner needle pointed downward. In another embodiment, insertion of the introducer is with the bevel of the inner needle pointed upward. In yet another embodiment, insertion of the introducer is with the bevel of the inner needle at an intermediate angle between upward and downward.

The exemplary embodiment described below (block 2010) is based on the use of a support structure including, at least, a vacuum chamber including proximal (3007) and distal (3009) elevated protrusions.

Figure 3C:
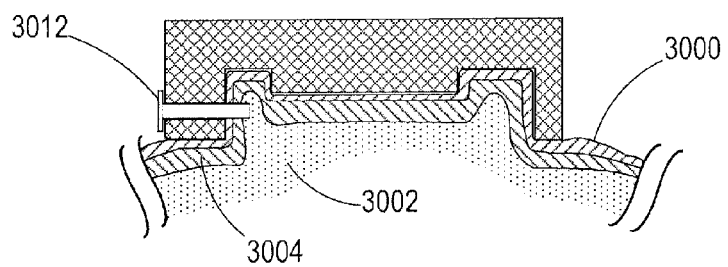

As indicated at block 2010 and FIG. 3C, the outer sleeve of the introducer, 3012, is positioned by inserting the introducer through the inner guide channel, through the epidermal 3000 and dermal 3004 layers of the skin-related structure and into the fat layer 3002 located under the proximal protrusion. Following insertion of the introducer, the inner needle is withdrawn from the skin-related structure and the outer sleeve remains in place, such that the distal end of the outer sleeve resides about mid-way under the proximal protrusion. The result of this action is that the outer sleeve is positioned coaxially with the inner guide channel, which may also be the cutting axis, and the tip of the outer sleeve extends into the fat (3002) of the skin-related tissue structure supported by the proximal protrusion 3007.

The outer sleeve, 3012, may be made up of a thin tube, a hollow rod, or any other suitable thin, generally straight, object able to be placed around the inner needle and able to penetrate the necessary skin layers. For example, in one embodiment, an outer sleeve may have an inner diameter which corresponds with a needle of size 12-19 GA for example, about 14 GA. In one embodiment, an outer sleeve may include a plastic tube of an appropriate length. In one embodiment, the outer sleeve includes high-density polyethylene (HPDE) tubing. In another embodiment, the outer sleeve includes polytetrafluoroethylene (PTFE) tubing. In another embodiment, the outer sleeve includes fluorinated ethylene propylene (PEP) tubing. In one embodiment the length of the outer sleeve is approximately 10-100 mm. In one embodiment, the length of the outer sleeve is approximately 40 mm. In one embodiment, approximately 5-20% of the length of the outer sleeve enters the skin-related structure beyond the puncture site. In one embodiment, approximately 10-15% of the length of the outer sleeve enters the skin related structure beyond the puncture site. In one embodiment, approximately 12.5% of the length of the outer sleeve enters the skin-related structure beyond the puncture site.

The embodiments above describe penetration of an outer sleeve into a fat layer. In another embodiment, an outer sleeve may be inserted into dermis tissue. In yet another embodiment, an outer sleeve may be inserted into a subcutaneous space.

The length of penetration of the outer sleeve 3012 through the skin into dermis or fat or a subcutaneous space may generally correspond to 1 to 15 mm, or in one embodiment about 5 mm. For example, an outer sleeve may be inserted manually as part of the introducer, and guided to a desired depth within the dermis, fat or subcutaneous tissue under the proximal protrusion. The outer sleeve is then co-axial with the cutting axis within the central channel, so that dermis may be harvested by the cutting tool.

In one embodiment, use of an outer sleeve protects an entry puncture site from exposure to the rotational and forward motion of a cutting tool, thereby preventing additional trauma to the skin at the site of entry.

Figure 3D:
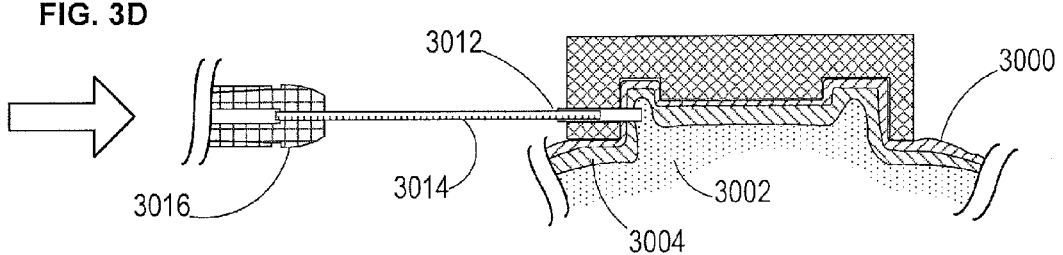
Figure 3E:
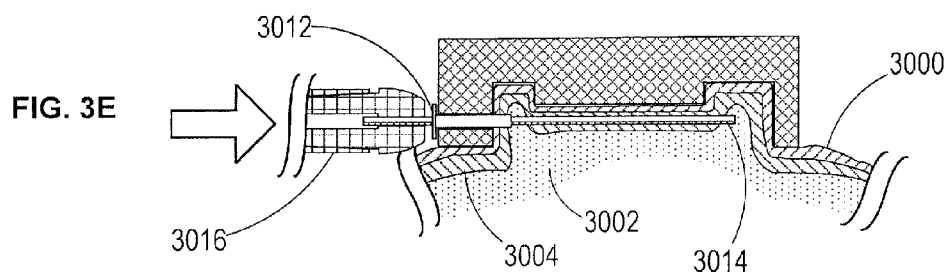

As indicated at block 2012 and FIGS. 3D and 3E, a DMO may now be cut from the skin-related tissue. A cutting tool, 3014, may be inserted coaxially through the guide channel 3008 and outer sleeve 3012, such that the outer sleeve guides the cutting tool along a cutting axis (FIG. 5A and FIG. 6) into the skin-related structure. In one embodiment, guiding a cutting tool through the outer sleeve may allow the cutting tool to directly enter dermal tissue (3004) of the skin-related structure (3E). As an aide to cutting, the cutting tool may be rotated as the tube advances towards the distal end of the apparatus. A motor may be used to rotate the cutting tool. A motor may be, for example, a pneumatic motor drill or an electric motor drill. In some embodiments, a medical drill may be used to rotate the cutting tool. In one embodiment, the cutting tool attaches at one end to a drill collet (3016), as is known in the art In one embodiment the method may include rotating the cutting tool while advancing the cutting tool, e.g., towards the distal end of the support structure. For example, a medical drill or other suitable tool or rotation mechanism may be used to rotate a coring tube 3014 while it is advanced manually or automatically, thereby more smoothly cutting dermal tissue for a DMO. For example, a proximal end of coring tube may be connected to a medical drill using a drill collet, 3016. Examples of medical drills include the Aesculap Micro Speed drill manufactured by Aesculap AG & Co. KG, Am Aesculap Platz, D-78532 Tuttlingen, Germany, which may include a control unit, a motor, a connection cord, a hand piece and/or a foot switch, catalogue numbers GD650, GD658, GB661, GB166 and GB660, respectively; and a Nouvag medical drill, TCM-3000-BL, and hand piece, catalogue numbers 3285 and 1710, respectively. Such a drill, or any other suitable drill or rotation mechanism, may be used to rotate the cutting edge of the cutting tool at a rotational speed appropriate for cutting of the dermal tissue, for example, a relatively high rotational speed, for example, a speed higher than 1,000 RPM, e.g., between 1,000 RPM and 10,000 RPM. For example, tube 3014 may be rotated at a rotational speed higher than 2,000 RPM, e.g., approximately 7,000 RPM. Alternatively, a relatively low rotational speed of less than 1000 RPM may be used, or no rotation at all, as described below. Optionally, the rotational speed of the drill may vary in an oscillatory manner, i.e., the direction of rotation may vary periodically between "clockwise" and "counterclockwise" directions. While rotated by a drill, a coring tube may be manually or automatically advanced, e.g., towards the distal end of the support structure, e.g., towards the distal elevated protrusion 3009.

In one embodiment, a method of cutting a dermal micro-organ may include stopping the forward motion of the coring tube at a particular location. In one embodiment, the meeting of the collet of the drill (3016) with the proximal end of the introducer sleeve (3012) at the outer surface of a support structure (3006) may act as a hard stop, preventing further forward motion of a coring tube. In another embodiment, the meeting of or an element placed on the external distal portion of the coring tube, e.g., a cap encircling the coring tube (FIG. 13; 1302), with the outer surface of a support structure may act as a hard stop, preventing further forward motion of a coring tube.

In certain exemplary embodiments, a method of cutting a DMO using a support structure including a vacuum chamber with at least a distal elevated protrusion may include stopping the forward motion of coring tube, for example, at a position such that the tip of the coring tube (FIG. 3E) has been advanced to reside within the region of the skin-related structure positioned under the distal elevated protrusion 3009. In one embodiment, the meeting of the collet of the drill with the introducer sleeve at the outer surface of a support structure may position the distal tip of the coring tube in fat. In one embodiment, the meeting of the collet of the drill with the introducer sleeve at the outer surface of a support structure may position the distal tip of the coring tube to reside under the distal elevated protrusion such that the tip enters the fat layer.

In one embodiment, the geometry of the skin-related structure created within a vacuum chamber with at least a distal elevated protrusion ensures that at termination of forward movement the distal tip of a coring tube will have crossed the dermis/fat interface, so that the tip resides in fat. The dermis/fat interface has a weak connection. In one embodiment, the weak connection between dermis and fat may ensure that the dermal tissue sample can be separated from the body fat during recovery of the DMO.

The cutting tool may include any suitable cutting tool, for example, a coring tube (e.g., FIG. 4E; 4010). Coring tube may include a generally symmetrically sharpened tubular tool, e.g., a hypodermic tube processed to have sharpened cutting edge with a desired shape. A coring tube may include, for example, a standard medical grade tube, having a thin wall, e.g., having a thickness of between 0.05 mm and 0.3 mm. A coring tube may have an inner diameter, for example, between 0.5 mm-4 mm. In one embodiment, an inner diameter may be between 1-2 mm. In another embodiment, an inner diameter may be between 1-3 mm. In yet another embodiment, an inner diameter may be between 2-4 mm. In still another embodiment, an inner diameter may be between 0.5-1.5 mm. In one embodiment, an inner diameter may be about 1.21 mm. In another embodiment, an inner diameter may be about 1.5 mm. In still another embodiment, an inner diameter may be about 1.71 mm. In yet another embodiment, an inner diameter may be about 2 mm. In one embodiment, the coring tube has about the dimensions of a 14 GA needle. In another embodiment, the coring tube has about the dimensions of a 12 GA, 13 GA, 15 GA, 16 GA, 17 GA, 18 GA or 19 GA needle. The dimensions, e.g., the diameter, of coring tube and/or the dimensions of introducer may be predetermined based on the volume and/or dimensions of the DMO intended to be harvested. A coring tube may have a sharpened end ("tip") adapted to serve as a cutting edge. In one embodiment, the sharpened edge is sharpened on the outer diameter. In another embodiment, the sharpened edge is sharpened on the inner diameter. A coring tube may be inserted through the outer sleeve and into the skin-related tissue structure in order to prevent harvesting of epidermal tissue. In one embodiment, use of a support structure with at least a proximal elevated protrusion creates a precise geometry of the skin-related structure when under vacuum conditions such that an epidermal layer and/or a plug of epidermis is not harvested.

According to some exemplary embodiments of the invention, at least part of an inner surface and/or an outer surface of tube may be coated with a low friction material, e.g., Teflon®, Parylene or any other suitable coating material, e.g., to ease the separation of the harvested tissue from the inner surface of the cutting tool in a subsequent action and/or to reduce any forces acting on the tissue during the cutting action, as described below.

Figure 3F:
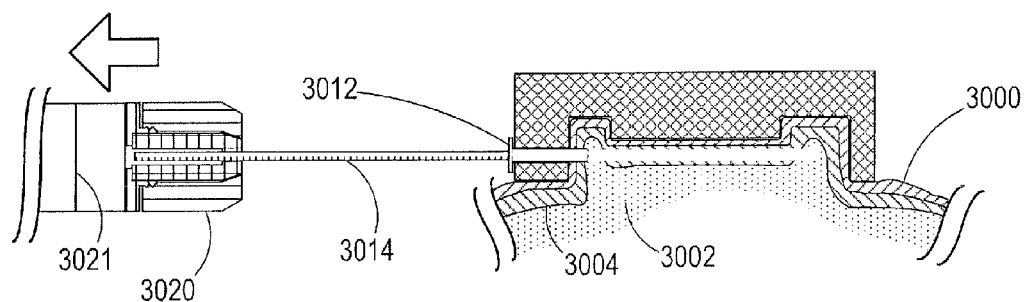
Figure 3G:
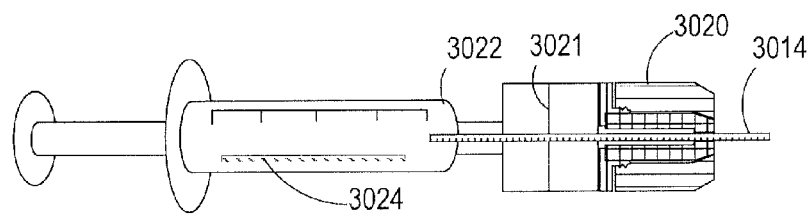

As indicated at block 2014 and FIGS. 3F and 3G, the method of harvesting includes recovery of the DMO 3024. After a coring tube has been advanced to a hard-stop and the distal tip of the coring tube is located within the skin-related tissue structure positioned under the distal elevated protrusion (e.g., FIG. 6), the collet of the drill 3016 (FIG. 4H) is opened and while holding the coring tube in place, the drill is removed. In one embodiment, an external cap, for example a luercap, may be use to hold the coring tube in place. Then the collet 3020/septum 3021 of the syringe 3022 assembly is attached (FIGS. 4B, 4A (4004) and 4 (4012), respectively) to the coring tube.

In one embodiment, a male luercap (1302) is attached, e.g., glued, to the outer surface of a coring needle (1304). The ability to hold the glued cap in place while removing the drill and connecting the syringe, prevents movement of the coring needle during the final steps of harvesting of a DMO. This may prevent potential loss of a DMO.

First the collet 3020 is attached. This is a stand-alone collet, not that of the medical drill. The collet may be slipped over the coring tube when in the open position. After the collet is in place and put in the closed position, the septum 3021 is pushed over the needle and attached to the collet. In one embodiment, the septum includes a needleless valve. In one embodiment, the needleless valve provides an airtight seal. The collet and septum together are referred to as a needleless valve assembly. The collet prevents the septum from pushing the coring tube forward during attachment of the septum. Once the septum is punctured by the coring tube and attached (e.g., by screwing) to the collet, the syringe 3022 can be attached to the needless valve assembly. When the syringe plunger is withdrawn there is creation of a vacuum condition within the coring tube. At this point, the entire assembly with the coring tube may be retracted (FIGS. 3F and 3G), which causes the cut tissue to be drawn into the syringe.

In one embodiment, a vacuum condition is applied at the same time as the coring tube is withdrawn from the skin-related tissue structure, and the DMO is collected for example, into the syringe body. In another embodiment, the coring tube is withdrawn from the skin-related tissue structure and then a vacuum condition is applied to the coring tube resulting in recovery of the DMO, for example, into the syringe body. In yet another embodiment, a vacuum condition is applied to the coring tube while the coring tube remains in the skin-related tissue structure and the DMO is recovered, for example, into the syringe body. In still another embodiment, a drill is disconnected from a coring needle (1304) while holding a glued cap (1302) in place. (FIG. 13) Then a female luer syringe (1306) is attached directly to the clued cap. When the plunger of the syringe is withdrawn and the syringe/coring needle assembly retracted from the skin-related tissue structure, the DMO is suctioned directly into the syringe body. Connection of the coring tube with the syringe using a leurcap eliminates the need for a collet and needleless valve assembly.

In one embodiment, the syringe is partially filled with saline or other suitable liquid, such that the tissue sample is withdrawn into a fluid environment which supports tissue viability.

The septum 3021 is needed to make sure that there is an air-tight connection between the syringe 3022 and the interior of the coring needle. If the syringe is attached to the collet directly without a septum, withdrawal of the plunger of the syringe would not cause a vacuum condition in the coring tube since a collet is in general not airtight. FIG. 4A (4012) shows one embodiment of a septum which may in certain embodiments be used in a method of harvesting a DMO of this invention.

In still another embodiment, recovery of a DMO is achieved by withdrawing the cutting tool, from the skin-related structure, wherein the DMO is retained within the cutting tool. The DMO 3024 may then be recovered from the cutting tool using positive pressure, e.g., the proximal end of the cutting tool may be attached to a syringe and positive pressure applied by a syringe plunger so that a DMO is "pushed" from the distal end of the cutting tool. In addition, suitable fluids, such as sterile fluids, may be used to assist in removing the DMO from cutting tool 3014.

In yet another embodiment, a DMO may be, for example, carefully removed from a cutting tool using mechanical means, such as tweezers or similar tools, which can be used to grasp the distal end of the DMO located at the distal end of the cutting tool.

As indicated at block 2016, the apparatus may then be removed from the harvest site. At this time, the outer sleeve may be removed manually from the skin-related tissue.

It will be appreciated by those skilled in the art that any combination of the above actions may be implemented to perform harvesting according to embodiments of the invention. Further, other actions or series of actions may be used.

Reference is also made to FIGS. 4C-E, which present exemplary embodiments of a harvesting apparatus, wherein FIG. 4C presents an example of a support structure attached to a vacuum source; FIG. 4D presents an example of an introducer, inner guide needle (4006) and outer sleeve (4008—white tube); FIG. 4E (4010) presents an example of a coring tube; and 4014 presents an example of a medical drill useful for rotating a cutting tool, and 4012 presents an example of a drill collet for attaching the coring tube. FIGS. 4A-B present exemplary embodiments of a syringe (FIG. 4A (4012)), septum (FIG. 4A 4004) and syringe collet (FIG. 4B) for use in the recovery of a dermal micro-organ.

According to some embodiments of the present invention, the above described manual procedures may be facilitated by an integrated apparatus (not shown) configured to perform some or all of the above procedures for harvesting the DMO. For example, in regard to one harvesting method embodiment, the integrated apparatus may be configured to enable positioning and guiding the insertion of an introducer FIG. 4D, guiding the insertion of coring tube FIG. 4E 4010 and controlling its rotational and forward movement during the cutting process, and/or removing DMO from a coring tube. Such an apparatus may enable relatively simple operation when performing a harvesting procedure.

Reference is now made to FIG. 5A, which schematically illustrates a dermal harvesting apparatus 5000 according to another exemplary embodiment of the invention. As used herein, the term "support structure" refers to the body of the apparatus used to support a skin-related tissue structure. The term "support structure" may also be referred to herein as an "apparatus". In this context an "apparatus" has all the qualities and properties of a "support structure".

Apparatus 5000 may include a guide channel 5003 and a vacuum chamber 5001 including an elevated protrusion 5006. Elevated protrusion 5006 may have a predetermined size and/or shape adapted, for example, to enable the creation of a "plateau" of a single layer of skin tissue in a generally flat orientation, elevated above the trajectory of a coring tube 5016. For example, section 5006 may be higher than other sections of chamber 5001, such that a fat layer 5018 may be drawn into section 5006 and supported along the trajectory of coring tube 5016. As a result, after harvesting a DMO of a predetermined length, coring tube 5016 may be advanced into fat layer 5018, thus separating the harvested DMO from tissue surrounding the DMO. The harvested DMO may remain within coring tube 5016 as it is withdrawn from the body, or a vacuum condition may be applied to the proximal end of the coring tube to suction the DMO from the coring tube. The configuration of Apparatus 5000 may eliminate the need for forming an "exit" incision in the skin, thus enabling the harvesting of a DMO with only a single incision.

According to some exemplary embodiments of the invention, apparatus 5000 may also include a drill stopper 5008 to enable manually advancing coring tube 5016 for a predetermined distance along chamber 5001, e.g., to a position in which coring tube 5016 has advanced into fat tissue 5018.

According to some exemplary embodiment of the invention, apparatus 5000 may also include a vacuum conduit 5004 which is connected to the vacuum chamber 5001 and a vacuum source 5002.

Figure 5B:
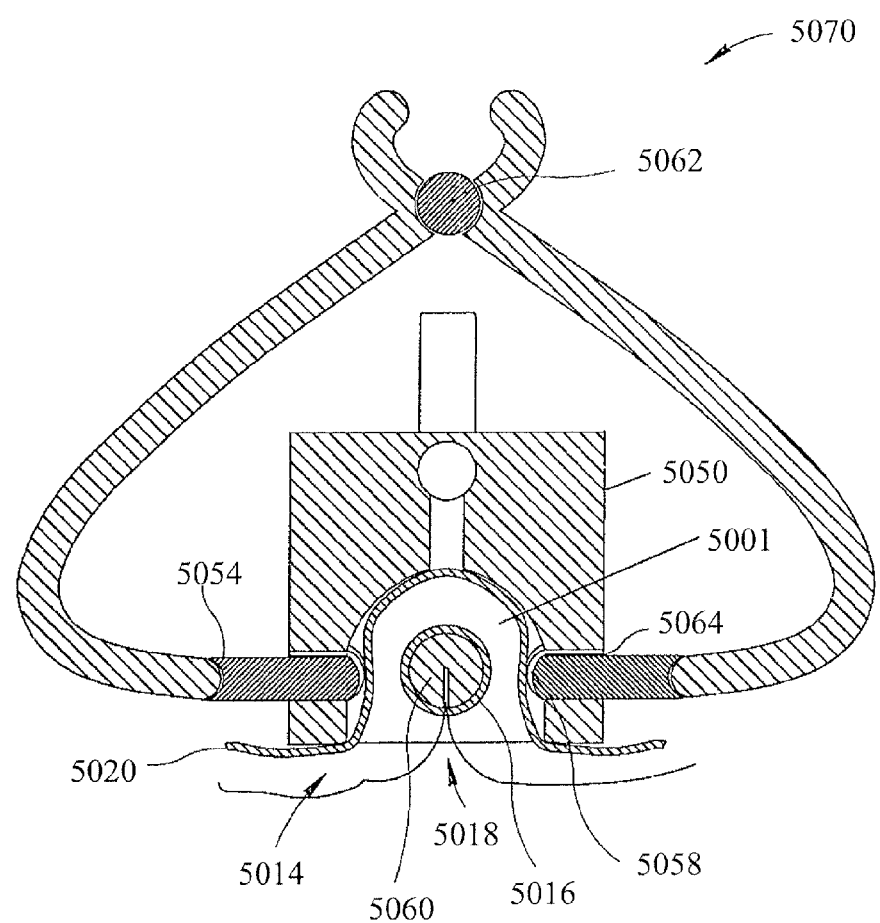

Reference is now made to FIG. 5B, which schematically illustrates a cross-sectional side view of a harvesting apparatus 5050 being implemented for externally supporting a skin-related tissue structure at a desired position according to another exemplary embodiment of the invention.

In some embodiments, apparatus 5050 may include two channels 5064 located at least partially along two sides of chamber 5001, respectively, to allow clamping epidermis layer 5020. Channels 5064 may be positioned, e.g., centered, at a desired height, for example, at approximately the same height as where the center of the DMO is to be harvested. In one embodiment, the central channel may be positioned at a height of about 2 mm below upper surface of the vacuum chamber. so that the clamping may stabilize and/or support the tissue being cut. According to these exemplary embodiments, apparatus 5050 may also include two flexible membrane elements 5058, on either the inner surface or outer surface of channels 5064, so as to allow external clamping of the tissue without substantially affecting the vacuum condition applied to chamber 5001. According to other embodiments of the invention, apparatus 5050 may not include elements 5058 and/or channels 5064.

According to the exemplary embodiment of FIG. 5B, improved stabilization of dermis 5014 and/or improved prevention of recruitment of fat 5018 into vacuum chamber 5001 may be accomplished by external clamping of the skin-related tissue structure supported within the vacuum chamber. For example, a clamping tool 5070, may be implemented to "pinch" the skin-related tissue structure supported inside vacuum chamber 5001, e.g., symmetrically. Two clamping ends 5054 of clamping tool 5070 may be inserted into channels 5056, respectively. Tool 5070 may be closed such that clamping ends 5054 may press down against flexible elements 5058. Thus, the skin-related tissue structure in chamber 5001 may be clamped from the sides without substantially affecting the vacuum condition in chamber 5001. A clamping force applied by clamping ends 5054 may correspond, for example, to a constant or variable force of a spring 5062 or other suitable device.

Reference is now made to FIG. 6 and FIG. 11, which schematically illustrate embodiments of harvesting apparatuses according to some exemplary embodiment of the invention.

Apparatus 6000 may include a guide channel 6003 (FIG. 11, 1108) and a vacuum chamber 6001 (FIG. 11, 2030) including two elevated protrusions 6007 (proximal) and 6006 (distal) (FIG. 11, 1107 and 1109, respectively), and a central channel between the two protrusions. The apparatus 6000 may further include one or more vacuum channels and a vacuum conduit 6004 (FIG. 11, 1126) to fluidically connect the vacuum chamber with at least one vacuum source 6002. Elevated protrusions 6006 and 6007 may have a predetermined size and/or shape adapted, for example, to enable the creation of a "plateau" of a single layer of skin tissue in a generally flat orientation, elevated above the trajectory of a coring tube 6016. Elevated protrusions 6006 and 6007 may or may not have the same size and shape. For example, section 6006 and 6007 may be higher than other sections of chamber 6001, such that epidermal 6020, dermal 6060 and fat layers 6018 may be drawn into sections 6006 and 6007, respectively, such that in some embodiments, dermal tissue layers 6060 are supported within the central channel within the trajectory of the coring tube 6016.

Application of a vacuum condition to an apparatus including a vacuum chamber including two elevated protrusions, for example, creates a precise geometry of the skin-related tissue structure so that dermal tissue is harvested and a complete epidermal skin layer is not harvested. The presence of the proximal elevated protrusion in combination with use of the introducer avoids the harvesting of a plug of epidermal tissue at the proximal end of the DMO. After harvesting a DMO of a predetermined length, a coring tube 6016 may be advanced into a fat layer 6018, thus allowing separation of the harvested DMO from tissue surrounding the DMO. The harvested DMO may remain within coring tube 6016 as it is withdrawn from the body, or a vacuum condition may be applied to the proximal end of the coring tube to suction the DMO from the coring tube.

The configuration of Apparatus 60000 may eliminate the need for forming an "exit" incision in the skin, thus enabling the harvesting of a DMO with only a single puncture site.

According to some embodiments of the invention, the internal width of a vacuum chamber of apparatus 5000 and/or 6000 is about 3.5 mm. In one embodiment, a central channel may have a width of, for example, about 4 mm. In another embodiment, a central channel may have a width of, for example, 3.0 mm. Furthermore, in some embodiments, a central channel may have a height, excepting of the protrusions, of, for example, about 5 mm. In other embodiments, other ranges, such as for example, 3-25 mm, may also be used for the width and/or height of central channel, for example, any desired dimensions in the range of 3-25 mm may be used in some embodiments of the invention. The length of central channel may be generally similar to the length of the DMO being harvested, for example, approximately 30 mm in length; however, other ranges, for example, in the range of 5-100 mm. In another embodiment, the dimensions of the channel length may be, for example, about 10-60 mm in length. In another embodiment, the dimensions of the channel length may be, for example, about 20-60 mm in length. In another embodiment, the dimensions of the channel length may be, for example, about 20-50 mm in length. In another embodiment, the dimensions of the channel length may be, for example, about 20-40 mm in length. In another embodiment, the dimensions of the channel length may be, for example, about 20-100 mm in length. In another embodiment, the dimensions of the channel length may be, for example, about 30-100 mm in length. In another embodiment, the dimensions of the channel length may be, for example, about 40-100 mm in length. In another embodiment, the dimensions of channel length may be, for example, about 50-100 mm in length. In another embodiment, the dimensions of the channel length may be, for example, about 60-100 mm in length. In another embodiment, the dimensions of the channel length may be, for example, about 70-100 mm in length. In another embodiment, the dimensions of the channel length may be, for example, about 80-100 mm in length. In another embodiment, the dimensions of the channel length may be, for example, about 90-100 mm in length. In another embodiment the length may be around 20 mm. In another embodiment, the length may be about 30 mm. In another embodiment, the length may be about 40 mm.

Prior to actual harvesting of the DMO, an apparatus of 6000 may be used in conjunction with an introducer that includes, for instance, an inner needle and an outer sleeve (FIG. 4D, 4008) for puncturing the skin and inserting a portion of an outer sleeve through the skin at the puncture site and into fat tissue to prevent harvesting of epidermal tissue. Such an introducer may be inserted through a guide channel 6003 of apparatus 6000, wherein the tip of the outer sleeve reaches the area of proximal elevated protrusion 6006 and the tip of the needle extends beyond the distal end of the outer sleeve. In one embodiment, the tip of the outer sleeve passes through the skin layers and into the fat layer. In one embodiment, the inner needle is a 14 GA needle. In another embodiment, the inner needle is a 12 GA needle. In another embodiment, the inner needle is a 13 GA needle. In another embodiment, the inner needle is a 15 GA needle. In yet another embodiment, the inner needle is a 16 GA needle. In still another embodiment, the inner needle is a 17 GA needle. In another embodiment, the inner needle is an 18 GA needle. In another embodiment, the inner needle is a 19 GA needle.

As a result of withdrawing the inner needle, the outer sleeve may reside and extend from within the guide channel 6003 into dermal tissue 6060. Alternatively, the outer sleeve may reside and extend from within the guide channel 6003 into fat tissue 6018. In one embodiment, an outer sleeve may be located from approximately the site of insertion to approximately the center of the proximal elevated protrusion 6007. The outer sleeve may act as a "sleeve" through which the coring needle may be introduced directly into the fat and immediately in front of the dermal tissue which is to be harvested. The outer sleeve thereby prevents harvesting of epidermal tissue. In another embodiment, the outer sleeve may act as a "sleeve" through which the coring needle may be introduced directly into the dermis, which is to be harvested. In addition, the outer sleeve protects the puncture site from the rotation and forward movement of the coring needle to prevent additional trauma to the puncture site. In certain instances, the outer sleeve may have a low coefficient of friction to prevent resistance to the rotational and forward motion of the coring needle, thereby preventing unwanted heat generation.

According to some exemplary embodiments of the invention, apparatus 6000 may also include a drill collet 6008 or glued cap to act as a hard stop enabling manual advancing of a coring tube 6016 for a predetermined distance along chamber 6001, e.g., to a position in which coring tube 6016 has advanced into fat tissue 6018 within distal elevated protrusion 6006.

Tool 6016 may be connected to a motor, e.g., as described above, to rotate tool 6016 at a rotational speed appropriate for cutting of the dermal tissue, for example, a relatively high rotational speed, for example, a speed higher than 1,000 RPM, e.g., between 1,000 RPM and 10,000 RPM. For example, tool 6016 may be rotated at a rotational speed higher than 2,000 RPM, e.g., approximately 7,000 RPM. When complete, the forward and rotational movements of tool 6016 may be stopped, and cutting tool 6016 may be retracted with harvested DMO within it, thereby removing the cutting tool from the harvest site. DMO may be removed from cutting tool 6016, e.g., using a syringe to flush sterile fluid, for example saline, through tool, or a vacuum source to draw out DMO from a back end (not shown) of cutting tool 6016, as described above.

It will be appreciated by those skilled in the art that apparatus 6000 may enable harvesting of the DMO by forming only one incision or puncture point. Furthermore, apparatus 6000 may be efficiently applied for harvesting a DMO from areas having relatively thick skin, e.g., from a region of the donor's back.

In some embodiments, elements of harvesting apparatus may be single use items.

Figure 10:
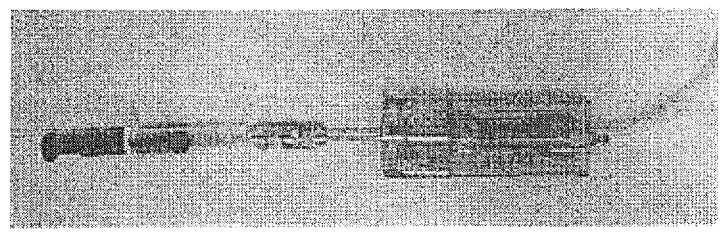
FIGS. 10A-B show embodiments of a syringe with a septum and collet.
Figure 10:
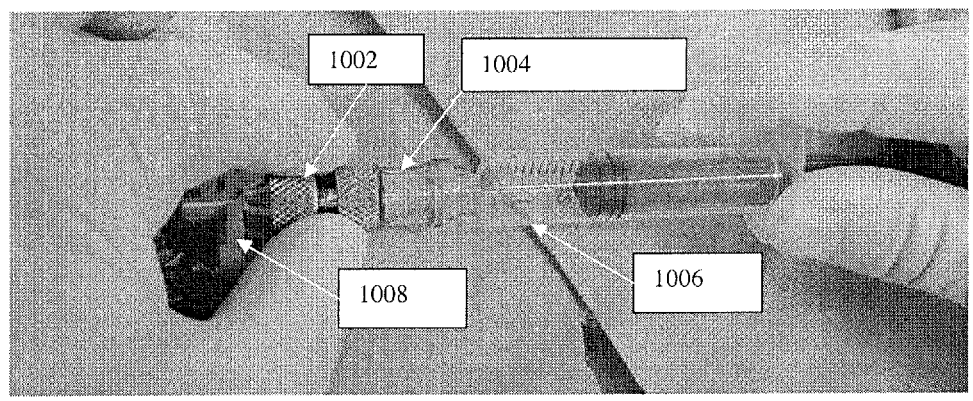

Reference is now made to FIGS. 10A and 10B, which show embodiments of a syringe with a septum and collet. FIG. 10A shows a syringe with a septum and collet attached to the back end of a cutting tool which is inserted through a support structure guide channel and an outer sleeve, wherein the support structure is connected to a vacuum source. FIG. 10B shows an embodiment of a syringe with a collet and needless valve attached to the back end of a coring needle.

FIGS. 10A and 10B illustrate an embodiment of the invention, wherein a female luer syringe is attached to the back end of the coring needle via a collet and needleless valve. FIGS. 10A and 10B illustrate embodiments that may be used in order to suction the DMO out of the cutting tool and into the syringe body.

It will be appreciated by those skilled in the art that the harvesting methods and/or apparatuses according to embodiments of the invention, e.g., as described above, may include introducing thin tissue cutting devices within the dermis. Thus, the harvesting methods and/or apparatuses according to embodiments of the invention may enable harvesting the DMO with relatively minimal damage to the outer skin surface, and therefore may provide a minimally invasive method of harvesting the desired tissues.

Although some embodiments of the invention described herein may refer to methods and/or apparatuses for harvesting a DMO, it will be appreciated by those skilled in the art that according to other embodiments of the invention at least some of the methods and/or apparatuses may be implemented for any other procedures, e.g., plastic surgical procedures, dermatological procedures, or any other procedures including harvesting of tissues. For example, the methods and/or apparatuses according to embodiments of the invention may be implemented for harvesting dermal tissue to be used, e.g., in a subsequent implantation, as filler material.

According to some embodiments of the present invention, a system and method are provided for ex-vivo ("in vitro") handling or processing of dermal micro-organs. In some embodiments, the dermal MOs may be directly placed into tissue culture wells or transduction chambers of a bioreactor, for further processing. In some embodiments, e.g., if the DMO remains in the coring tube as it is withdrawn from the skin, the DMO may be flushed out of the coring tube by the use of biologically compatible fluid, e.g., saline or growth medium, applied to the back end of the coring tube. The flushing of the DMO may to be such that it is flushed directly into a chamber of a bioreactor. Alternatively, vacuum may be applied to a back end of the coring tube to "draw out" the DMO, e.g., directly into a chamber of a bioreactor.

II. Methods and Apparatuses for Implanting a DMO/DTMO

According to some embodiments of the present invention, a system and method are provided for implantation of DTMOs. After producing and/or processing of a DMO, for example, by genetically modifying the DMO, the modified DMO or DTMO may be implanted back into the patient, for example, for protein or RNA based therapy. The number of full or partial DTMOs that are implanted may be determined by the desired therapeutic dosing of the secreted protein. DTMOs may be implanted subcutaneously or into dermal tissue or at other locations within the body. Subcutaneous implantation by use of an implantation needle, for example, may enable the DTMO to remain in a linear form in a subcutaneous space. The linear form of implantation may help facilitate localization in case later removal or in-situ ablation of the DTMO is required, for example, in order to stop treatment or reduce the dose of therapeutic protein. Other known geometrical implantation patterns could be used. The linear implantation may also assist in the integration of the dermal tissue to the surrounding tissue.

Figure 7:
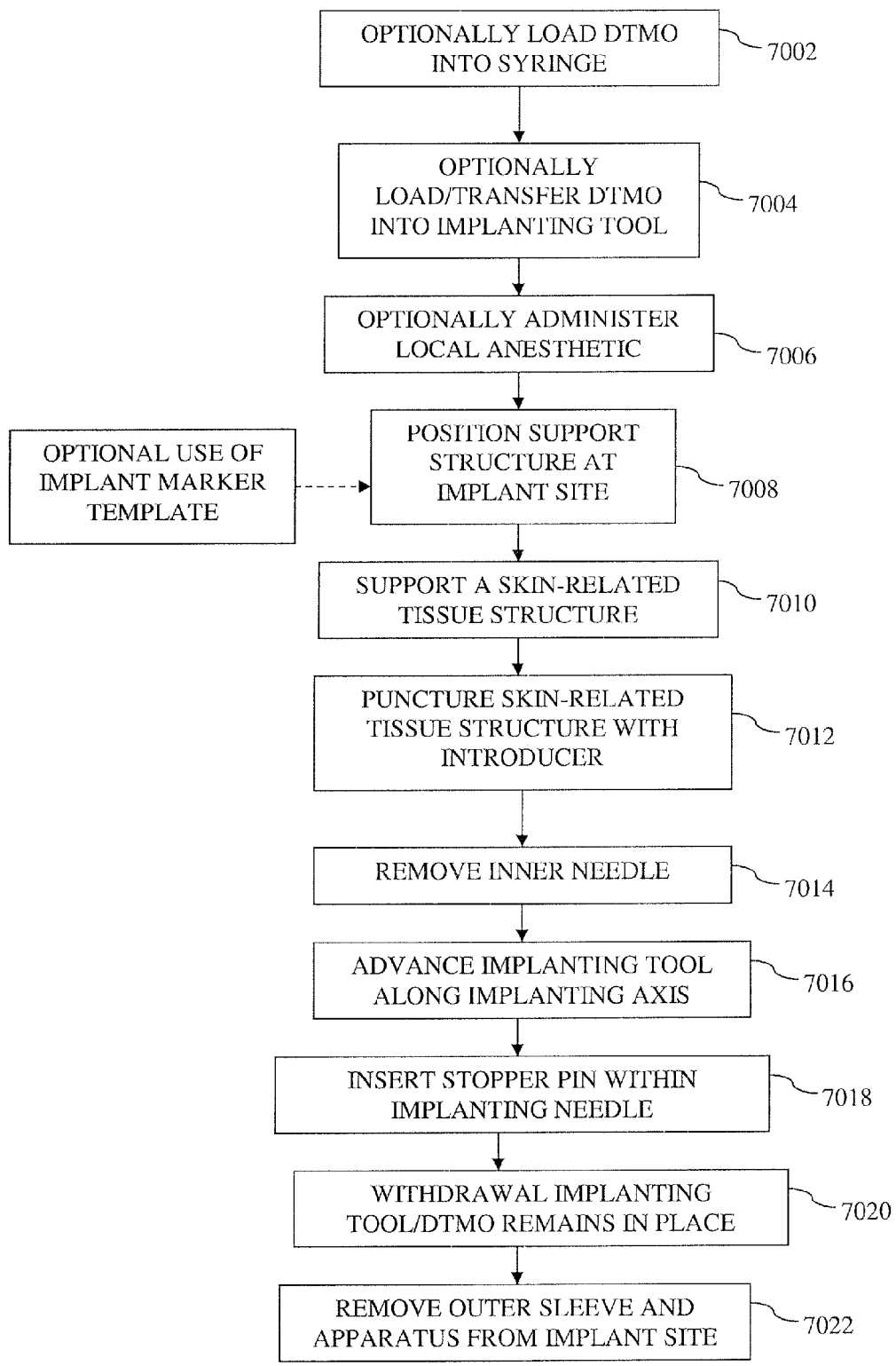
FIG. 7 is a flow chart illustrating a DTMO implanting method, according to some exemplary embodiments of the present invention.

Reference is now made to FIGS. 7, 8A-E and 9A-E. FIG. 7 schematically illustrates a flowchart of a method of implanting a DMO/DTMO according to some exemplary embodiments of the invention, and to FIGS. 8A-E, which present some embodiments of elements of an implanting apparatus. The methods of implantation presented herein refer to implantation of either a DMO or a DTMO, and the terms may be used interchangeable in describing the methods and apparatus for implantation. For ease of reading only, a DTMO is recited in the description below wherein it is recognized that the term "DMO" is interchangeable with the term "DTMO" in the following description.

Figure 8:
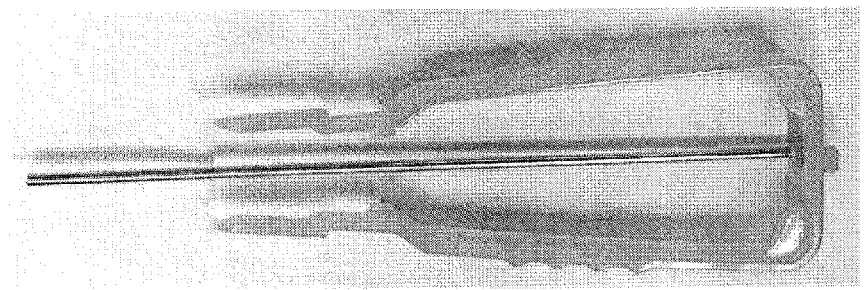
FIGS. 8A-E show an embodiment of an implanting apparatus. 8A is an embodiment of a loading syringe, 8B is an embodiment of an implanting tool, 8C is an embodiment of an introducer, 8D is an embodiment of a support structure, and 8E is an embodiment of a stopper.
Figure 8:
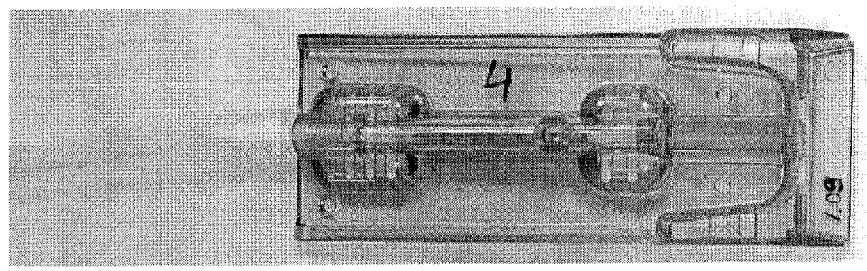
Figure 8:
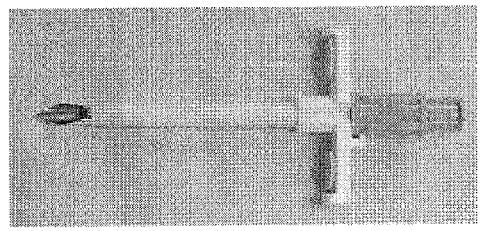
Figure 8:
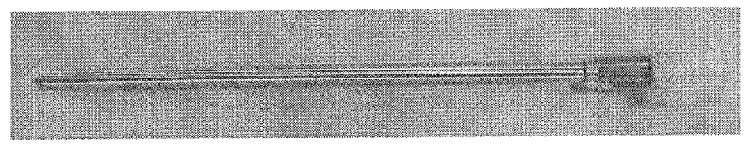
Figure 8:

As indicated at block 7002, a DTMO may be loaded into a syringe (FIG. 8A). For instance a DTMO may be aspirated into a loading syringe. Loading may entail drawing up biologically compatible fluid, e.g., saline or growth medium. Following loading of the DTMO in the syringe, an implanting tool, for example an implantation needle (FIG. 8B), may be attached to the syringe.

As indicated at block 7004, according to some exemplary embodiments of the invention, the DTMO, optionally together with surrounding sterile saline fluid may be loaded into an implanting tool (FIG. 8B) by connecting a loading syringe containing the DTMO with the proximal end of an implantation needle, and then gently loading the DTMO into the needle using positive pressure. Alternatively, a DTMO may be aspirated directly into an implantation needle, for example, through the distal end of an implantation needle by withdrawing a plunger of a syringe attached to the proximal end of an implantation needle. Optionally, a tip of the needle may have a removable short extension of silicon tubing, or the like, affixed to it, to facilitate the aspiration of the DTMO into the needle cannula through the distal end while retracting the plunger of the syringe.

An implantation needle may have any suitable diameter, for example, between 17 GA and 8GA. In one embodiment, the diameter of an implanting tool is about that of a 10 GA needle. In some embodiments, the tip of an implanting tool has a beveled edge. In other embodiments, the tip of an implanting tool does not have a beveled edge.

In some embodiments, after loading the DTMO into the implantation needle, the proximal (back) end of the implanting needle is plugged to prevent the DTMO from coming out the back end of the tube. In other embodiments, an adjustment of positive/negative pressure using the plunger of the loading syringe is used to keep the DTMO within the implanting needle.

As indicated at block 7006 a local anesthetic may be optionally administered, e.g., as is known in the art, to the vicinity of an intended implantation site.

As indicated at block 7008, the method may further include positioning an apparatus including a support structure (FIG. 8D), at a given implantation site so that the support structure is in contact with an epidermal surface of the subject. In some embodiments, contact between a support structure of this invention and the epidermal surface of a subject must be air-tight so that a vacuum seal may be formed at a later step. In one embodiment, an implantation site is on a subject's abdomen. In another embodiment, an implantation site is on a subject's back. Alternatively, the implantation site may be at another location on the subject's body.

In some instances, dosage may be adjusted based on the number/size/efficacy of DTMOs to be implanted. For example, multiple DTMOs may be implanted consecutively during a single procedural time period in order to reach a target dose. In one embodiment, an implant marker template may be used prior to positioning an implanting apparatus on a subject's epidermal surface (step 7008), in order to mark multiple sites for implanting. In one embodiment, an implanting marker template is positioned on the epidermal surface of a subject, and the epidermal surface is then marked to indicate, for example, anesthesia lines and alignment lines for later placement of the support structure 9006. In one embodiment, the surface is marked using a surgical pen or marker. In one embodiment, the surface is marked using a non-permanent dye or ink.

As indicated at block 7010, a support structure FIG. 8D, which may include a vacuum chamber with at least one elevated protrusion and guide channel 9008, wherein the elevated protrusion, 9007, is adjacent to the guide channel. For instance a support structure of FIG. 5A or 5B may be used to hold and support the skin-related tissue structure in place for proper implanting of a DTMO, for example, to create a unique geometry of the skin, such that the path of implantation is precisely controlled. For example, application of vacuum conditions causes a vacuum to be formed within the vacuum chamber thereby drawing the epidermal surface of the skin-related structure into the interior of the support structure, wherein a central channel may support epidermal and dermal skin layers, and possibly fat layers, of the skin-related structure. In exemplary embodiments, a vacuum condition may cause the skin-related structure to be held at an inner support surface of the vacuum chamber. The guide channel may provide guidance and/or stability for an implanting tool to ensure proper implanting along a linear implanting axis, which in one embodiment is in the subcutaneous space, such as between the dermis and fat layers. In some embodiments, implanting results in a DTMO remaining substantially linear after implantation. In some embodiments, the implanting axis is coaxial with the needle guide channel and central channel. In another embodiment, a DTMO is implanting without ensuring linearity.

Figure 9A:
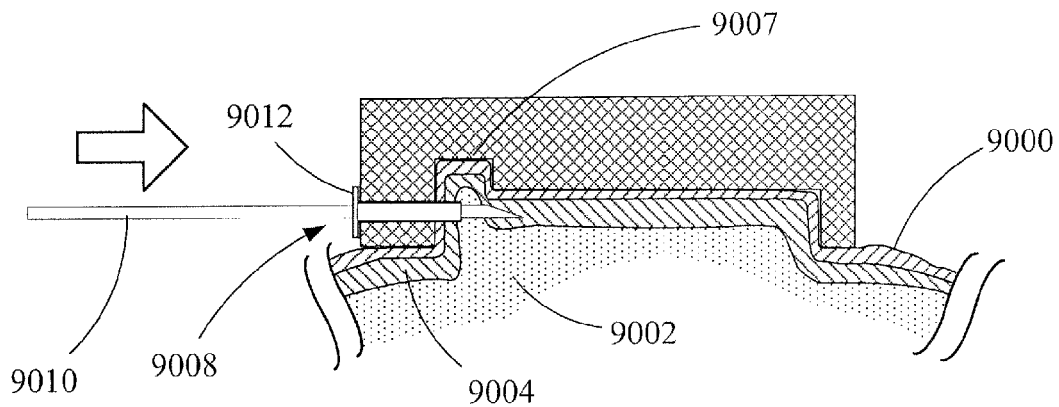
FIG. 9A-E are schematic illustrations of exemplary stages of implanting a DTMO in accordance with a method of FIG. 7.
Figure 9B:
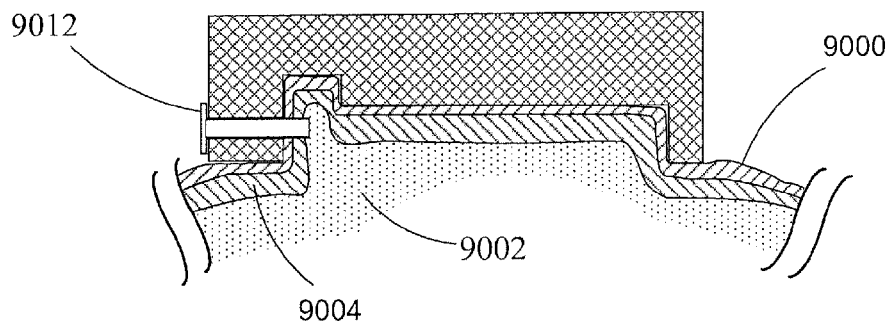

As indicated at block 7012 and FIGS. 9A and 9B, and similar to the use for methods of harvesting described above, an introducer, FIG. 8C, may then be used to puncture the skin-related tissue by inserting the introducer through the guide channel of the support structure and into the skin-related structure along the implanting axis. This single puncture site may be used for all further entry into the skin-related structure. In this way damage and scarring to the subject is limited. In addition, use of an introducer eliminates exposure of the loaded DTMO within an implantation tool to a vacuum condition while implantation tool is penetrating the skin-related structure. Exposure of the DTMO loaded in the implantation needle to vacuum conditions present within the support structure may lead to a risk of the DTMO being suctioned into the vacuum line.

An introducer composed of an inner needle 9010 and an outer sleeve 9012, fitted as a sheath over the inner needle, may be inserted into the skin-related structure such that the distal edge of the outer sleeve extends into the region of tissue just under the elevated protrusion. Under vacuum conditions, a precise geometry of the skin-related tissue structure is created such that insertion of the introducer is for example, generally perpendicular to the skin surface at the point of penetration. In one embodiment, the inner needle of the introducer and the implanting tool have about the same dimensions of diameter. For instance, the diameter of an inner needle and of an implanting tool may each be about those of a 10 GA needle.

As indicated at block 7014 and FIG. 9B, the inner needle is withdrawn from the skin-related tissue structure while the outer sleeve component 9012 of the introducer is positioned and remains in place. The result of this action is that the outer sleeve is positioned coaxially with the implanting axis and extends into the skin-related tissue structure. In preferred embodiments, the distal edge of the outer sleeve extends into the fat under the elevated protrusion. In other preferred embodiments, the distal edge of the outer sleeve extends into dermis under the elevated protrusion.

The outer sleeve may include a thin needle, tube or any other suitable thin, generally straight, object able to be placed inside the dermis or in a subcutaneous space. For example, an outer sleeve may include a needle of size 6-18 GA, for example, about 10 GA or 14 GA, as is known in the art. Alternatively, an outer sleeve may include a plastic tube. In one embodiment, an outer sleeve includes high-density polyethylene (HDPE) tubing. In another embodiment, an outer sleeve includes Teflon®. In yet another embodiment, an outer sleeve includes polytetrafluoroethylene (PTFE) tubing. In still another embodiment, an outer sleeve includes fluorinated ethylene propylene (PEP) tubing.

An introducer may be inserted into the dermis or subcutaneous space by being pushed generally perpendicular to the skin surface at the point of penetration. In one embodiment, an inner needle is beveled. In such a circumstance, introduction of the inner needle part of an introducer may be with the bevel side facing down. In another embodiment, the bevel side is facing upward. In yet another embodiment, the bevel side is facing any direction in between upward and downward. In still another embodiment, an inner needle is not beveled.

Figure 9C:
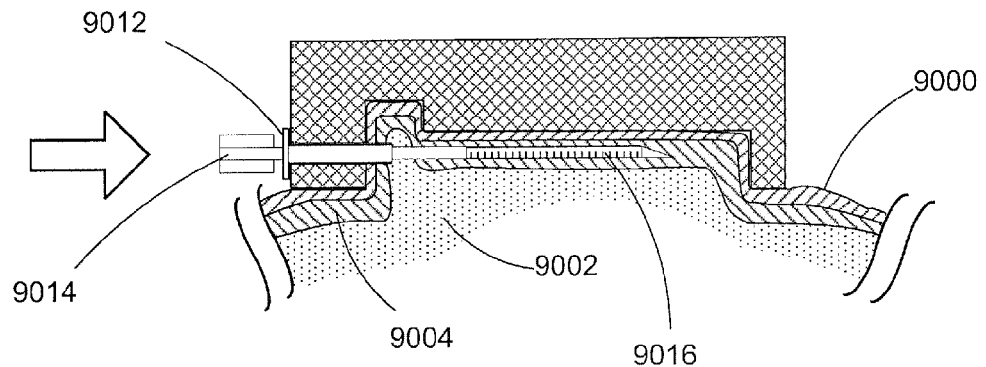

As indicated at block 7016 and FIG. 9C, an implanting tool 9014 with the loaded DTMO 9016 may be inserted through the support structure guide channel and the outer sleeve, and advanced along an implanting axis into the desired location, e.g., in the subcutaneous space, within a fat layer, at the interface of fat layer and dermis layer, or into dermal tissue layer, along a distance approximately equivalent to the length of the DTMO. A silicon tubing extension, if used for loading of the DTMO 1716, would be removed prior to insertion of the implanting tool through the needle guide channel. An implanting tool may be a needle, for instance 6 GA-14 GA. In one embodiment, an implanting tool may be a 10 GA needle. In another embodiment, an implanting tool may be a 14 GA needle. In one embodiment, the implanting tool is inserted with the bevel up. In another embodiment, the implanting tool is inserted with the bevel down. Once the implanting tool has been advanced for placement of a DTMO at a desired location, the plug at the proximal end of the implanting tool, if used, is removed.

Figure 9D:
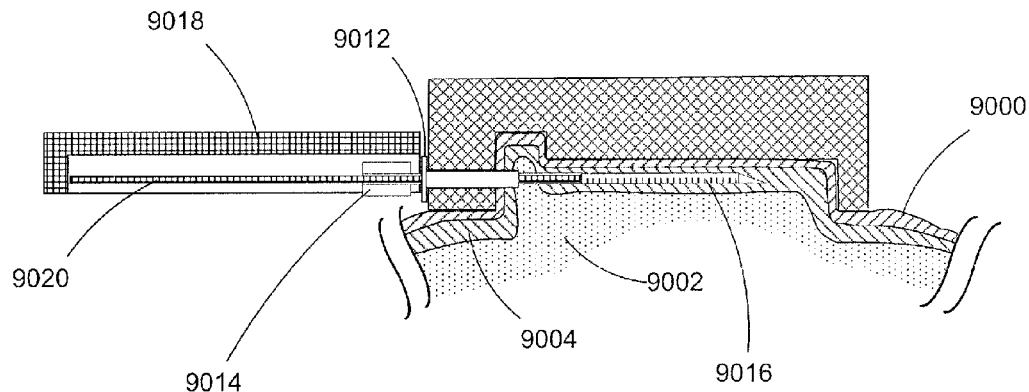

As indicated at block 7018 and FIG. 9D, a stopper tool including a stopper tool body 9018 and a stopper pin 9020 (FIG. 8E) may be connected with an apparatus such that it is secured relative to the apparatus and a stopper pin inserts within the implanting needle 9016 through the proximal end.

Figure 9E:
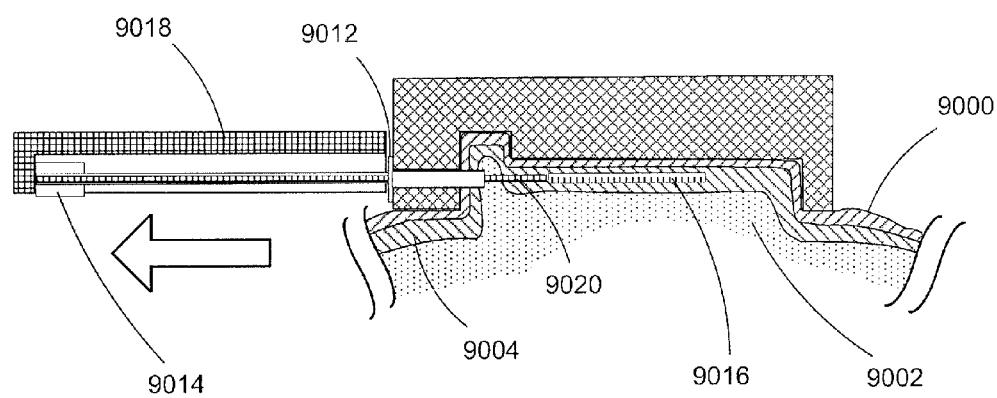

As indicated at block 7020 and FIG. 9E, the implantation needle may be retracted through e.g., the subcutaneous space, releasing the DTMO from the implantation needle and laying the DTMO linearly along the needle tract. In one embodiment, in order to ensure linear placement of a DTMO, a stopper pin, 9020, of a stopper tool (FIG. 8E) is inserted within the proximal end of the implanting needle. In another embodiment, assistance may be given to help release the DTMO for example by connecting a syringe to the proximal end of the implantation needle and gently providing positive pressure with the syringe plunger, possibly during retraction of the implantation needle.

In exemplary embodiments of the invention, a stopper of FIG. 8E is attached to the support structure FIG. 8D, such that the rod of the stopper is internal and coaxial with the implanting tool. In one embodiment, the stopper's association with the support structure is such that its placement is set, e.g., locked-in-place, relative to other elements of the implanting apparatus. For instance, the stopper rod may fit inside the back end of the implanting needle such that the rod is brought into close proximity with the loaded DTMO within the implanting needle, and the implanting needle may be withdrawn over the stationary rod of the stopper. Retraction of the implanting needle over the rod may, in one embodiment, be for the full extent of the rod. In another embodiment, retraction may be over a part of the rods length. As the rod is stationary, retraction of the needle may result in the rod extending beyond the beveled tip of the implanting needle after retraction. Retraction of the implanting needle over the rod of the stopper may in some instances prevent the DTMO from being pulled back together with the implanting needle. In yet another embodiment, retraction may result in the DTMO being released into the target site, e.g. subcutaneous space, in a linear form.

Linear implantation of a DTMO may provide better exposure of the implanted tissue to surrounding environment. For example, linear implantation may facilitate better integration of the DTMO. In addition, linear implantation may facilitate diffusion of a secreted recombinant product, e.g., a recombinant protein or portion thereof. Moreover, linear implantation may facilitate increased angiogenesis in the region of the DTMO. If, at a future date, it is required that a DTMO be excised or ablated, linear positioning provides a known orientation and location of a given DTMO. In one embodiment, implantation results in a DTMO being placed linearly within a subcutaneous space. In another embodiment, implantation results in a DTMO being placed linearly within a tissue of the same kind as the DTMO, e.g., dermal tissue. In yet another embodiment, implantation results in a DTMO being placed linearly deeper in the body.

As indicated at block 7022, the apparatus may then be removed from the implant site. In addition, the outer sleeve may be removed at this time.

It will be appreciated by those skilled in the art that any combination of the above actions may be implemented to perform implanting according to embodiments of the invention. Further, other actions or series of actions may be used.

In addition and without repeating the description and all of the embodiments of apparatuses 5000 and 6000 (FIGS. 3-7 and FIG. 11) described above as apparatuses for harvesting, e.g., support structures for harvesting a DMO, in some embodiments of the invention apparatuses 5000 and 6000 may also be used in methods of implanting a DTMO. Accordingly, in some embodiments of the invention, apparatuses 5000 or 6000 may also be used in methods of implanting.

III. Methods and Apparatuses for Excising a DMO/DTMO

According to some embodiments of the present invention, a system and method are provided for in-vivo demarcation and localization of the implanted dermal micro-organs. Identification of the location of a subcutaneous implantation or implantation at any other location in the body, of processed tissue, such as a DTMO, may be important, for example, in the case where it is necessary to stop the protein treatment, or to decrease the dosage of the secreted protein. For example, termination or titration of dosage may be performed by removing one or more DTMOs entirely and/or by ablating one, a portion of one, or more than one of the implanted DTMOs. In order to identify a subcutaneously implanted DTMO, according to one embodiment, the DTMO may be colored prior to implantation by an inert, biocompatible ink or stain containing, for example, a chromophore, which may be visible to the naked eye or may require special illumination conditions to visualize it. In this way a DTMO may be distinguished from its surrounding tissue by visual inspection and/or by use of enhanced imaging means.

According to one embodiment, at least the peripheral surface of a DTMO may be coated with, for example, biocompatible carbon particles, biocompatible tattoo ink, or other suitable materials including titanium particles, magnetic particles and/or microspheres. Once implanted subcutaneously, the DTMO may be visible with the naked eye, by suitable enhanced imaging device, or other means of detection. Other ways to enhance the visibility of an implanted DTMO may include using a strong light source above the skin surface, or pinching the skin and directing the light source at the skin from one side, such that the skin may appear translucent and the dyed DTMO may be more visible. Alternatively, the stain may be fluorescent, visible only when illuminated using UV light, such as using fluorescent plastic beads.

According to another embodiment, the location of a subcutaneously implanted DTMO may be identified by co-implanting a biocompatible structure along with the DTMO. An example of such a biocompatible structure is a non-absorbable single stranded nylon suture commonly used in many surgical procedures. Such a suture may be implanted in the same implantation tract with the DTMO, or may be implanted directly above the DTMO in the upper dermis or below the DTMO in the fat, such that the spatial location of the DTMO may be determined by the suture location. Further, the depth of the DTMO may be known to be at the depth of the subcutaneous space. The suture may be visible to the naked eye, observed with the assistance of illumination means, and/or observed with the aid of other suitable imaging means, such as ultrasound. Alternatively, the suture can be fluorescent, and visible through the skin under appropriate UV illumination. The suture may alternatively be of an absorbable material, so that it may enable determination of localization for a desired period of time, such as a few months.

According to another embodiment, the DTMO may be genetically modified or engineered to include a gene to express a fluorescent marker or other marker capable of being visualized. For example, the DTMO can be modified with the GFP (Green Fluorescent Protein) gene or Luciferase reported gene, which, for example, may be expressed along with the gene for the therapeutic protein. In this manner, the DTMO may be visualized non-invasively using appropriate UV or other suitable illumination and imaging conditions.

According to another embodiment, one or more tattoo marks, e.g. small tattoo dots, can be applied on the skin in the vicinity of the implantation site. In a preferred embodiment, a small tattoo dot is applied to the skin at either end of a linearly implanted DTMO. The tattoo ink can be permanent, or temporary, such as ink used for cosmetic make-up use.

According to some embodiments of the present invention, a system and method are provided for removal or ablation of implanted DTMOs. In a case, for example, where DTMO-based therapy to a patient must be terminated, or if the protein secretion must be decreased, one or more implanted DTMO may be partially or entirely removed, or partially or entirely ablated. In one embodiment, the DTMO may be surgically removed.

According to one embodiment in which small tattoo dots are applied on the skin at either end of a linearly implanted DTMO, surgical excision of the DTMO can be accomplished by resection of an elliptical tissue sample, including at least both tattoo dots and including all of the layers of skin and some subcutaneous tissue to ensure that the DTMO has been removed. The excision site can then be sutured closed.

In addition and without repeating the description and all of the embodiments of apparatuses 6000 and 1100 (FIGS. 3-6 and 11) described above as apparatuses for harvesting, e.g., support structures for harvesting a DMO, in some embodiments of the invention apparatuses 6000 and 1100 may also be used in methods of excising a DTMO.

Figure 12:
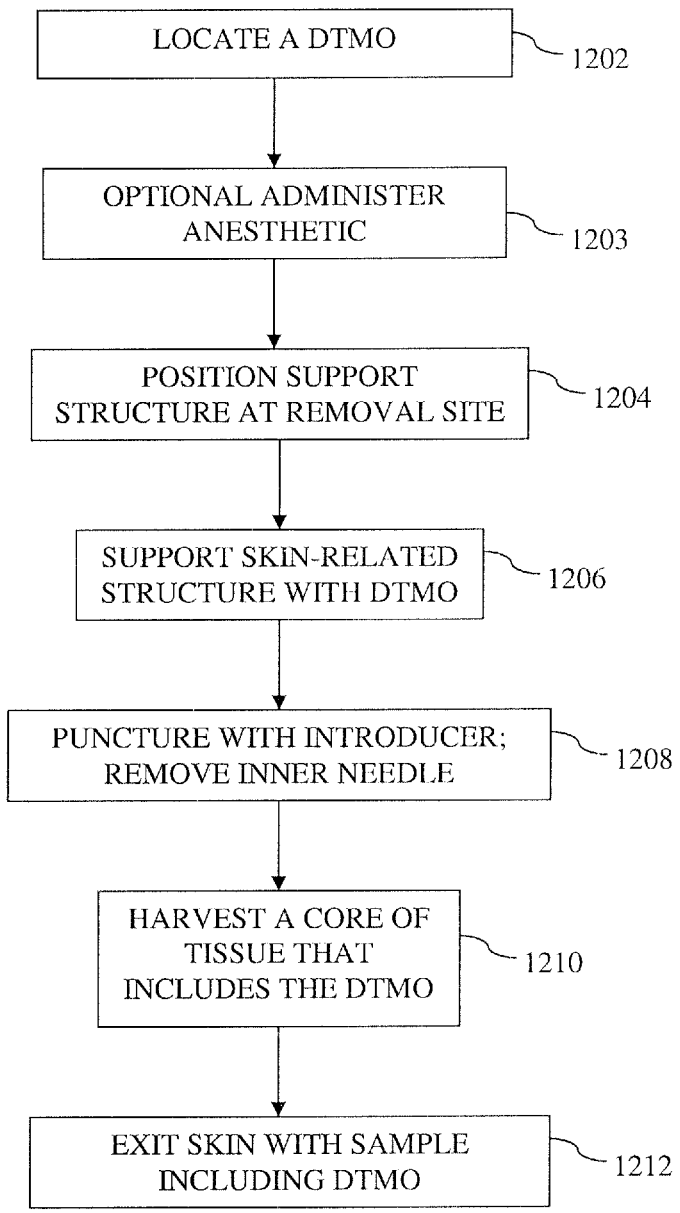
FIG. 12 is a flow chart illustrating a method of removing a previously implanted DTMO.

Reference is now made to FIG. 12, which illustrates an exemplary embodiment of excising a DTMO. It will be appreciated by those skilled in the art that any combination of the above actions for harvesting may be implemented to perform excising of an DTMO according to embodiments of the invention. Further, other actions or series of actions may be used.

Without repeating all of the embodiments for harvesting described in detail above, reference is now made to FIG. 12. Briefly, at block 1202 the location of the implanted subcutaneous DTMO may be determined. At block 1203, a local anesthetic may be optionally administered at the site of DTMO removal. At block 1204 a support structure may be positioned over the site of the DTMO to be removed. A support structure (e.g., FIG. 4C; FIGS. 5A-B, FIG. 6, FIG. 11), which may include a vacuum chamber and a guide channel, may be used to hold and support the skin-related tissue structure for proper excising of a DTMO and minimal surrounding tissue thereof.

At block 1206, vacuum conditions are applied and a skin-related tissue structure including the DTMO to be excised may be shaped so that the tissue containing the DTMO to be excised is within a central channel and is aligned with a cutting axis.

At block 1208, an introducer including an inner needle and an outer sleeve may be used to puncture the skin-related tissue by inserting the introducer through the guide channel of the support structure and into the skin-related tissue structure at a point of penetration. The inner needle is then removed and the outer sleeve remains positioned with the distal end of the outer sleeve residing in a region proximal to the DTMO to be excised.

At block 1210, a core of tissue that includes the DTMO may be harvested. A coring needle, of the same or larger diameter than that of the DMO harvesting needle (for example, 11 GA or similar), may be inserted through the guide channel and outer sleeve along a cutting axis in order to harvest the previously implanted DTMO. In one embodiment, a DTMO is excised using a coring tube similar to, or larger in diameter than that used for direct harvesting of the DMO. In one embodiment, additional tissue surrounding the DTMO being excised is harvested during the excision of the DTMO. In one embodiment, the additional tissue includes epidermal tissue. In one embodiment, the additional tissue includes dermal tissue not associated with the DTMO. In one embodiment, the additional tissue includes fat tissue. In one embodiment, such a coring approach may be combined with vacuum suction at the proximal end of the cutting tool to help remove the cut tissue sample from the body.

According to an embodiment of the present invention, minimally invasive or non-invasive methods of ablating the DTMO in-situ may be used to make the procedure less traumatic and less invasive for the patient. In one embodiment, potentially in conjunction with the case of the dyed DTMO, a laser, for example, a non-invasive Yag laser may be used. The energy of the Yag laser, for example, may be selectively absorbed by the chromophore of a dyed DTMO, such that the energy is primarily directed to the DTMO, with minimum damage caused to the surrounding tissue. Other light energy sources may also be used. Alternatively, such a laser approach can be used with other means of locating the DTMO other than use of a dye.

According to another embodiment, the DTMO may be ablated by delivering destructive energy from a minimally invasive probe inserted into the subcutaneous space along the length of the DTMO. Such a probe may enable delivery of a variety of energy types, including radio frequency, cryogenic temperatures, microwave, resistive heat, etc. A co-implanted structure, such as a suture, may be used to determine the location of the DTMO, thereby enabling the probe to be inserted subcutaneously, for example, along or directly above or below the suture. In such a case, for example, the destructive energy may be delivered while the suture is still in place. Alternatively, the suture may be removed after placement of the probe and before delivery of the destructive energy. The amount of energy applied may be either that required to denature the proteins in the tissue such as during coagulation by diathermy. Additionally or alternatively, the amount of energy applied may be as much as is used in electro-surgical cutting devices, which char tissue. Of course, other means of localization and other means of delivering destructive energy may be used.

IV. Methods and Apparatuses for Processing a DMO

After a DMO is harvested, e.g., according to embodiments of the present invention, the DMO is optionally genetically altered. Methods and Apparatuses for processing a DMO have been described in detail in United States Publication No. US-2012/0201793-A1, which is incorporated herein by reference in full.

In one embodiment, the invention provides a method of delivering a gene product of interest into a subject by implanting the genetically modified DMO of the invention into a subject.

The invention contemplates, in one aspect, the use of the genetically modified DTMO for transplantation in an organism. As used herein the terms "administering", "introducing", "implanting" and "transplanting" may be used interchangeably and refer to the placement of the DTMO of the invention into a subject, e.g., an autologous, allogeneic or xenogeneic subject, by a method or route which results in localization of the DTMO at a desired site. The DTMO is implanted at a desired location in the subject in such a way that at least a portion of the cells of the DTMO remain viable. In one embodiment of this invention, at least about 5%, in another embodiment of this invention, at least about 10%, in another embodiment of this invention, at least about 20%, in another embodiment of this invention, at least about 30%, in another embodiment of this invention, at least about 40%, and in another embodiment of this invention, at least about 50% or more of the cells remain viable after administration to a subject. The period of viability of the cells after administration to a subject can be as short as a few hours, e.g., twenty-four hours, to a few days, to as long as a few weeks to months or years.

Alternatively, the DTMO, which includes genetically modified cells can be kept in vitro and the therapeutic agent, left in the supernatant medium surrounding the tissue sample, can be isolated and injected or applied to the same or a different subject.

Alternatively or additionally, a DTMO can be cryogenically preserved by methods known in the art, for example, without limitation, gradual freezing (0° C., −20° C., −80° C., −196° C.) in DMEM containing 10% DMSO, immediately after being formed from the tissue sample or after genetic alteration.

In accordance with an aspect of some embodiments of the invention, the number of DTMOs to be implanted is determined from one or more of: Corresponding amounts of the therapeutic agent of interest routinely administered to such subjects based on regulatory guidelines, specific clinical protocols or population statistics for similar subjects. Corresponding amounts of the therapeutic agent such as protein of interest specifically to that same subject in the case that he/she has received it via injections or other routes previously. Subject data such as weight, age, physical condition, clinical status. Pharmacokinetic data from previous tissue sample which includes a genetically modified cell administration to other similar subjects. Response to previous DTMO administration to that subject.

In accordance with an aspect of some embodiments of the invention, only some of the DTMOs are used in a given treatment session. The remaining DTMOs may be returned to maintenance (or stored cryogenically or otherwise), for later use.

There is also provided in accordance with an embodiment of the invention, method of adjusting the dosage of a therapeutic agent produced by a DTMO implanted in a subject and excreting a therapeutic agent, including (a) monitoring level of therapeutic agent in the subject; (b) comparing the level of agent to a desired level; (c) if the level is lower than a minimum level, then implanting additional DTMO; (d) and if the level is higher than a maximum level, then ablating or removing one or more of the implanted DTMOs. Optionally, the method includes periodically repeating (a)-(d). Alternatively or additionally, ablating or removing consists of ablating or removing a portion of one or more of the implanted DTMOs. Optionally, removing includes surgical removal. Optionally, ablating includes killing a portion of the implanted DTMO.

As described above with reference to FIG. 1, at least part of the process of sustaining the DMO during the genetic alteration, as well as the genetic alteration itself, may be performed in a bioreactor.

EXAMPLES

Example 1

Harvesting of a Dermal Micro-Organ

Dermal micro-organs were harvested from a human subject under sterile conditions.

Experimental Procedure

With the subject prone, a harvest site on the lower abdomen was selected, disinfected, marked with guidelines, and injected with local anesthesia. The harvest site was in an area of healthy skin, free of stretch marks or other obvious skin abnormalities. A sterile harvesting support (FIG. 4C) structure containing a vacuum control hole was connected to a vacuum source, the vacuum turned on and the support structure placed on the subject's epidermis at the selected harvest site with the vacuum control hole uncovered.

A finger was placed over the vacuum control hole causing a vacuum to raise the skin-related tissue structure into the vacuum chamber.

With the sharpened bevel point of the Introducer inner needle facing down (FIG. 4D, 4006), the Introducer (4006 and 4008) was inserted into the needle guide of the support structure, quickly and to the full stop. The Introducer's inner needle 4006 was then removed, leaving behind the Introducer sleeve 4008.

Next the sharpened tip of the coring needle attached to the medical drill was inserted into the Introducer sleeve and gently pushed forward until the tip reached the distal end of the sleeve. The drill was then activated and pushed forward to the full stop, pushing the tip of the coring needle through the dermal tissue and into fat tissue. At this point the vacuum was deactivated by removing the finger from the vacuum control hole.

The drill was then disconnected from the coring needle and the needleless valve syringe assembly was connected to the coring needle by slipping the collet onto the needle and tightening it onto the needle, and then by piercing the septum with the exposed end of the coring needle and connecting that to the collet. The syringe was connected to the septum and the plunger of the syringe was withdrawn to create a vacuum, while the syringe was retracted together with the coring needle. The DMO was suctioned into the syringe body during this withdrawal process (FIG. 3G).

Experimental Results

Figure 14:
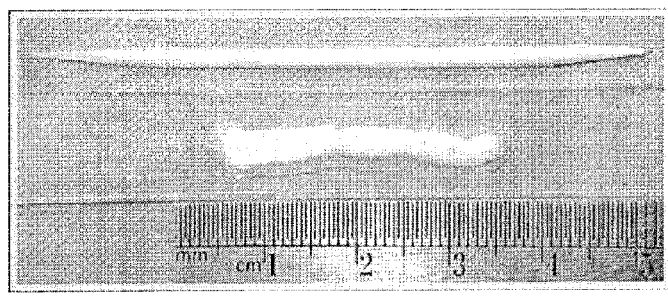
FIGS. 14A and 14B show embodiments of a harvested dermal micro-organ (FIG. 14A) and harvesting (1402) and implanting (1404) sites on a human subject.
Figure 14:
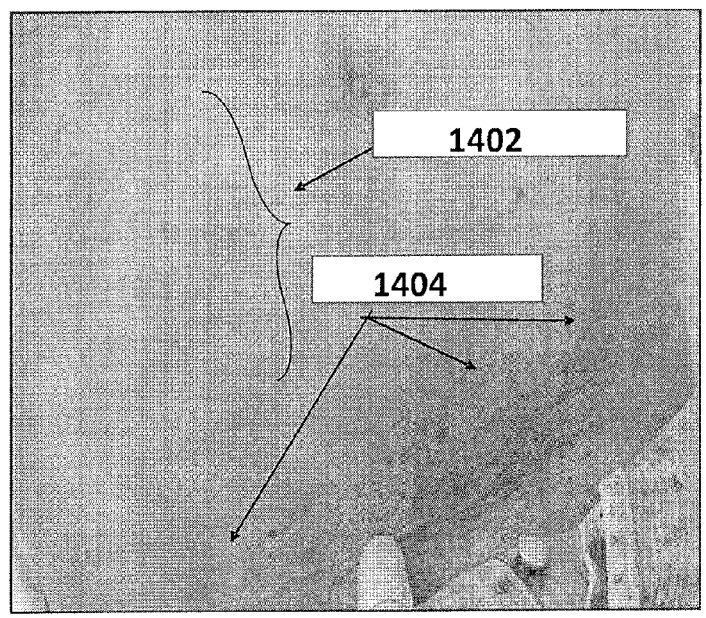

Multiple DMOs were harvested. An isolated harvested DMO is shown in FIG. 14A in comparison to a toothpick, wherein the DMO is approximately 30 mm in length. As shown in FIG. 14B (1402), there was only minimal scarring of the skin tissue at the harvest sites.

Example 2

Implanting of a Dermal Micro-Organ

Dermal micro-organs were implanted into a human subject under sterile conditions.

Experimental Procedure

Similar to preparations for harvesting, the implantation of dermal micro-organs into a human subject began with the subject prone, with implant sites selected on the lower abdomen, disinfected, marked with guidelines to align the support structure for implanting, and the sites injected with local anesthesia. A sterile implanting support structure (FIG. 8D) containing a vacuum control hole was connected to a vacuum source, the vacuum turned on and the support structure placed on the subject's epidermis at the marked implantation sites with the vacuum control hole uncovered.

A finger was placed over the vacuum control hole causing a vacuum to raise the skin-related tissue structure into the vacuum chamber.

With the sharpened bevel point of the Introducer inner needle facing down (FIG. 8C), the Introducer was inserted into the needle guide of the support structure, quickly and to the full stop. The Introducer's inner needle was then removed, leaving behind the Introducer sleeve.

Next the implantation needle loaded with a DMO at the distal end was inserted into the Introducer sleeve, and pushed forward to the full stop. The stopper element was than connected to the implanting apparatus by inserting the stopper pin within the inner lumen of the implantation needle. The stopper pin was moved forward and brought into close proximity to loaded DMO within the implantation needle. The stopper body was affixed to the implanting support structure so that the stopper pin remains stationary while the implantation needle was retracted over the stopper pin and the DMO was linearly implanting within the subcutaneous space at the implantation site.

The implanting tools were carefully removed from the implant site and the vacuum was removed by removing the finger from the vacuum hole. A tattoo dot was made with semi-permanent ink on the surface of the skin at either end of the linearly implanted DMO to demark the location of the implantation site.

Experimental Results

Multiple DMOs were implanted. As shown in FIG. 14B, DMOs were implanted in the lower abdomen (1404), wherein tattoo dots identify their site of implantation. There was only minimal scarring of the skin tissue at the implantation sites.

It will thus be clear, the present invention has been described using non-limiting detailed descriptions of embodiments thereof that are provided by way of example and that are not intended to limit the scope of the invention. For example, only a limited number of genetic changes have been shown. However, based on the methodology described herein in which live tissue is replanted in the body of the patient, and the viability of that tissue in the body after implantation, it is clear that virtually any genetic change in the tissue, induced by virtually any known method will result in secretions of target proteins or other therapeutic agents in the patient.

Variations of embodiments of the invention, including combinations of features from the various embodiments will occur to persons of the art. The scope of the invention is thus limited only by the scope of the claims. Furthermore, to avoid any question regarding the scope of the claims, where the terms "comprise" "include," or "have" and their conjugates, are used in the claims, they mean "including but not necessarily limited to".

Further, as used herein, the term "comprising" is intended to mean that the system includes the recited elements, but not excluding others which may be optional. By the phrase "consisting essentially of" it is meant a method that includes the recited elements but exclude other elements that may have an essential significant effect on the performance of the method. "Consisting of" shall thus mean excluding more than traces of other elements. Embodiments defined by each of these transition terms are within the scope of this invention.

Further, as used herein, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

Further, as used herein, the term "a" or "one" or "an" refers to at least one. In one embodiment the phrase "two or more" may be of any denomination, which will suit a particular purpose.

Further, as used herein, the term "treatment" refers to both therapeutic treatment and prophylactic or preventative measures, wherein the object is to prevent or lessen a targeted pathologic condition or disorder. Thus, in one embodiment, treating may include directly affecting or curing, suppressing, inhibiting, preventing, reducing the severity of, delaying the onset of, reducing symptoms associated with a disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An apparatus for directly harvesting a dermal micro-organ from a subject comprising:
   (a) a support structure to support a skin-related tissue structure of a subject from which a dermal micro-organ is to be harvested, said support structure comprising;
      (i). a first tubular element comprising a site of insertion into the apparatus;
      (ii) a vacuum chamber comprising an inner support surface able to hold said skin-related tissue structure in a desired shape and position to enable a cutting tool to cut said dermal micro-organ directly from said skin-related tissue structure, wherein said first tubular element is connected to said vacuum chamber; and
      (iii) one or more vacuum channels to fluidically connect said vacuum chamber with at least one vacuum source;
   (b) an introducer; and
   (c) said cutting tool able to directly separate said dermal micro-organ from said skin-related tissue structure;
   wherein said dermal micro-organ is an explant of living tissue consisting essentially of a plurality of dermal components located below the epidermis and lacking a complete epidermal layer that substantially maintain the micro-architecture and three-dimensional structure of the dermal tissue from which they are obtained.

2. The apparatus of claim 1, wherein said vacuum chamber further comprises:
   (a) two elevated protrusions, a proximal elevated protrusion and a distal elevated protrusion relative to said site of insertion, said elevated protrusions able to support a plateau of epidermal and dermal skin layers from said skin-related tissue structure above the trajectory of said cutting tool; and
   (b) a central channel located between said two elevated protrusions, wherein said central channel supports said skin-related tissue structure under vacuum conditions, so that the dermal skin layer is within the trajectory of said cutting tool when said cutting tool is inserted in said first tubular element.

3. The apparatus of claim 2, wherein said first tubular element is configured to align said cutting tool coaxially into said central channel.

4. The apparatus of claim 1, wherein said introducer comprises a second tubular element and a fourth tubular element, wherein
   (a) said second tubular element inserts through said fourth tubular element and extends beyond the distal end of said fourth tubular element;
   (b) said second and fourth tubular elements together insert at said site of insertion coaxially within said first tubular element; and
   (c) said fourth tubular element remains coaxial and within said first tubular element upon withdrawal of said second tubular element.

5. The apparatus of claim 4, wherein said second tubular element comprises an inner needle and said fourth tubular element comprises an outer sleeve.

6. The apparatus of claim 4, wherein said cutting tool comprises a third tubular element able to be inserted at said site of insertion through said fourth tubular element that remains coaxial and within said first tubular element following the withdrawal of said second tubular element, wherein said cutting tool is substantially coaxially with said first tubular element, said third tubular element able to cut said dermal micro-organ from said skin-related tissue structure.

7. The apparatus of claim 6, wherein said third tubular element comprises a coring tube able to cut through said skin-related tissue structure when advance along a cutting axis, wherein said cutting axis is substantially coaxial with said first tubular element.

8. The apparatus of claim 7, wherein said coring tube comprises a rotatable coring tube attached to a power source.

9. The apparatus of claim 8, wherein said power source is selected from an electrical motor or an air driven turbine.

10. The apparatus of claim 7, wherein said coring tube is a coring needle with a symmetrically sharpened tip.

11. A method of directly harvesting a dermal micro-organ from a subject comprising the steps of:
   (a) positioning an apparatus of claim 1 at a harvest site in contact with an epidermal surface of said subject;
   (b) supporting a skin-related tissue structure of said subject at said harvest site from which a dermal micro-organ is to be harvested;
   (c) puncturing the skin-related tissue structure;
   (d) directly cutting said dermal micro-organ from said supported skin-related tissue structure; and
   (e) directly recovering said dermal micro-organ,
   wherein said dermal micro-organ is an explant of living tissue consisting essentially of a plurality of dermal components located below the epidermis and lacking a complete epidermal layer that substantially maintain the micro-architecture and three-dimensional structure of the dermal tissue from which they are obtained.

12. The method of claim 11, wherein said harvesting method comprises making only a single puncture point in said skin-related structure.

13. The method of claim 11, wherein said apparatus comprises:
  (a) a support structure to hold said skin-related tissue structure from which said dermal micro-organ is to be harvested, wherein said support structure comprises a first tubular element and a vacuum chamber, and wherein said first tubular element is a guide channel, which is substantially parallel with said epidermal surface of said subject, and wherein said guide channel is connected to said vacuum chamber;
  (b) an introducer comprising a second tubular element and a fourth tubular element, wherein said second tubular element comprises an inner needle and said fourth tubular element comprises outer sleeve, and said inner needle inserts through said outer sleeve and extends beyond the distal end of said outer sleeve; and
  (c) a cutting tool comprising a third tubular element able to be inserted into said outer sleeve positioned within and coaxially with said guide channel, wherein said third tubular element is a coring tube, which cuts said dermal micro-organ from said skin-related tissue structure.

14. The method of claim 13, wherein
  (a) said supporting comprises applying a vacuum condition to said vacuum chamber, wherein said vacuum condition causes said skin-related structure to be held at an inner support surface of said vacuum chamber;
  (b) said puncturing comprises inserting said introducer through said guide channel and into said skin-related structure followed by withdrawing said inner needle from said outer sleeve and from said skin-related structure, said outer sleeve remaining within said guide channel and within said skin-related structure; and
  (c) said cutting comprises inserting said coring tube through and coaxially within said outer sleeve, said coring tube entering said skin-related structure.

15. The method of claim 11, wherein said recovering comprises use of a vacuum to withdraw said dermal micro-organ from said coring tube into a closed container.

16. The method of claim 11, wherein said recovering comprises pushing said dermal micro-organ from said coring tube.

17. The method of claim 14, wherein said cutting further comprises the steps of:
  (a) rotating said coring tube, wherein said rotating coring tube is advanced towards the distal end of said apparatus; and
  (b) wherein said recovering further comprises withdrawing said coring tube from said skin-related structure while simultaneously applying a vacuum condition within said coring tube, said dermal micro-organ being withdrawn into a closed container.

* * * * *